United States Patent
Byrne et al.

(10) Patent No.: US 11,760,817 B2
(45) Date of Patent: *Sep. 19, 2023

(54) MASS POLYMERIZABLE POLYCYCLOOLEFIN COMPOSITIONS CONTAINING SOLUBLE PHOTOACID GENERATORS

(71) Applicant: PROMERUS, LLC, Akron, OH (US)

(72) Inventors: Paul D Byrne, Akron, OH (US); Brian Knapp, Akron, OH (US)

(73) Assignee: PROMERUS, LLC, Akron, OH (US)

( * ) Notice: Subject to any disclaimer, the term of this patent is extended or adjusted under 35 U.S.C. 154(b) by 247 days.

This patent is subject to a terminal disclaimer.

(21) Appl. No.: 17/341,850

(22) Filed: Jun. 8, 2021

(65) Prior Publication Data

US 2021/0380733 A1 Dec. 9, 2021

Related U.S. Application Data

(60) Provisional application No. 63/036,078, filed on Jun. 8, 2020.

(51) Int. Cl.
| | |
|---|---|
| *C08F 32/08* | (2006.01) |
| *C07F 5/02* | (2006.01) |
| *C07C 25/18* | (2006.01) |
| *C08F 2/50* | (2006.01) |
| *C07C 381/12* | (2006.01) |
| *C07C 309/06* | (2006.01) |
| *C07F 5/06* | (2006.01) |

(52) U.S. Cl.
CPC .............. *C08F 32/08* (2013.01); *C07C 25/18* (2013.01); *C07C 309/06* (2013.01); *C07C 381/12* (2013.01); *C07F 5/027* (2013.01); *C07F 5/069* (2013.01); *C08F 2/50* (2013.01)

(58) Field of Classification Search
CPC ..... C07C 25/18; C07C 309/06; C07C 381/12; C07F 5/022; C07F 5/027; C07F 5/269; C07F 7/0838; C07F 7/1804; C07F 15/0066; C07F 15/0086; C08F 2/50; C08F 32/08

See application file for complete search history.

(56) References Cited

U.S. PATENT DOCUMENTS

| | | | | |
|---|---|---|---|---|
| 5,403,869 | A | * 4/1995 | Arike | H05K 3/386 |
| | | | | 522/170 |
| 6,423,378 | B1 | 7/2002 | Cotting et al. | |
| 6,587,628 | B1 | 7/2003 | Walker | |
| 6,652,281 | B1 | 11/2003 | Eckhardt et al. | |
| 7,087,691 | B2 * | 8/2006 | Rhodes | C08F 20/12 |
| | | | | 526/329 |
| 8,916,624 | B2 | 12/2014 | Frances et al. | |
| 10,626,198 | B2 * | 4/2020 | Rhodes | C08F 32/08 |
| 2018/0194880 | A1 * | 7/2018 | Rhodes | C09D 145/00 |
| 2020/0377632 | A1 * | 12/2020 | Burtovyy | C08F 132/08 |
| 2021/0198392 | A1 * | 7/2021 | Deng | C08F 232/08 |
| 2021/0198393 | A1 * | 7/2021 | Deng | C08F 232/08 |
| 2021/0380733 | A1 * | 12/2021 | Byrne | C07F 5/022 |
| 2023/0038665 | A1 * | 2/2023 | Hayakawa | C08K 5/375 |

FOREIGN PATENT DOCUMENTS

| | | | | |
|---|---|---|---|---|
| JP | 1998-001507 A | 1/1998 | | |
| JP | 1998-153861 A | 6/1998 | | |
| JP | 1998-168341 A | 6/1998 | | |
| JP | 2012093396 A | * 5/2012 | | |
| TW | 539689 A | * 7/2003 | ............. | C08F 32/08 |
| WO | WO-0020472 A1 | * 4/2000 | ............. | C08F 32/00 |
| WO | WO-2018129121 A1 | * 7/2018 | ............. | C08F 2/38 |

* cited by examiner

*Primary Examiner* — Sanza L. McClendon
(74) *Attorney, Agent, or Firm* — Balaram Gupta

(57) ABSTRACT

Embodiments in accordance with the present invention encompass compositions comprising a soluble photoacid generator, a organopalladium compound, a photosensitizer and one or more olefinic monomers which undergo vinyl addition polymerization when said composition is exposed to a suitable actinic radiation to form a substantially transparent film. The monomers employed therein have a range of optical and mechanical properties, and thus these compositions can be tailored to form films having various opto-electronic properties. Accordingly, compositions of this invention are useful in various applications, including as coatings, encapsulants, fillers, leveling agents, among others.

20 Claims, No Drawings

MASS POLYMERIZABLE POLYCYCLOOLEFIN COMPOSITIONS CONTAINING SOLUBLE PHOTOACID GENERATORS

CROSS REFERENCE TO RELATED APPLICATIONS

This application claims the benefit of U.S. Provisional Application No. 63/036,078, filed Jun. 8, 2020, which is incorporated herein by reference in its entirety.

BACKGROUND OF THE INVENTION

Field of the Invention

Embodiments in accordance with the present invention relate generally to mass polymerizable polycycloolefin monomer compositions containing soluble photoacid generators having utility in such applications as optical sensors, light emitting diodes (LEDs), organic light emitting diode (OLED), among others. More specifically, this invention relates to single component compositions encompassing primarily non-polar norbornene (NB) based olefinic monomers, which undergo mass vinyl addition or ring open metathesis polymerization in the presence of soluble photoacid generators and palladium or ruthenium catalysts which when photolyzed forms optical layers having utility in a variety of opto-electronic applications including as encapsulants, coatings, and fillers.

Description of the Art

Organic light emitting diodes (OLEDs) are gaining importance in a variety of applications, including flat panel televisions and other flexible displays, among other applications. However, conventional OLEDs, particularly, bottom emitting OLEDs suffer from a drawback in that only about half of the generated photons are emitted into the glass substrate out of which 25% are extracted into air. The other half of the photons are wave-guided and dissipated in the OLED stack. This loss of photons is primarily attributed to the refractive index (n) mismatch between the organic layers (n=1.7-1.9) and the glass substrate (n=1.5). By matching the refractive index of the substrate (n=1.8) and organic layers and augmenting the distance of the emission zone to the cathode to suppress plasmonic losses light extraction into the substrate can be increased to 80-90%. See, for example, G. Gaertner et al., Proc. Of SPIE, Vol. 6999, 69992T pp 1-12 (2008).

In addition, OLEDs also pose other challenges; in that OLEDs being organic materials, they are generally sensitive to moisture, oxygen, temperature, and other harsh conditions. Thus, it is imperative that OLEDs are protected from such harsh atmospheric conditions. See for example, U. S. Patent Application Publication No. US2012/0009393 A1.

In order to address some of the issues faced by the art, U.S. Pat. No. 8,263,235 discloses use of a light emitting layer formed from at least one organic light emitting material and an aliphatic compound not having an aromatic ring, and a refractive index of the light emitting from 1.4 to 1.6. The aliphatic compounds described therein are generally a variety of polyalkyl ethers, and the like, which are known to be unstable at high temperatures, see for example, Rodriguez et al., I & EC Product Research and Development, Vol. 1, No. 3, 206-210 (1962).

U.S. Pat. Nos. 9,944,818 and 10,266,720, disclose a two component mass polymerizable composition which is capable of tailoring to the desirable refractive index and is suitable as a filler and a protective coating material, thus potentially useful in the fabrication of a variety of OLED devices.

U.S. Pat. No. 10,626,198 B2, discloses a single component mass vinyl addition polymerizable composition which is thermally activated and capable of tailoring to the desirable refractive index and is suitable as a filler and a protective coating material, thus potentially useful in the fabrication of a variety of OLED devices.

However, there is still a need for organic filler materials that complement the refractive index of OLEDs and yet exhibit high transparency and good thermal properties, among other desirable properties. In addition, it is desirable that such organic filler materials readily form a permanent protective coatings and are available as a single component composition for dispensing with such OLED layers simply by exposing to suitable actinic radiation at ambient temperature.

It has been observed in some of these compositions the photoacid generator which is generally employed to mass polymerize the cyclic olefinic monomer is not soluble in such compositions thus rendering the compositions unsuitable for a variety of applications.

Thus, it is an object of this invention to provide organic materials that overcome the gaps faced by the art. More specifically, it is an object of this invention to provide a single component composition that will mass polymerize when exposed to suitable actinic radiation under the conditions of the fabrications of an OLED device. It is further an object of this invention to provide stable single component mass polymerizable composition with no change in viscosity at or below normal storage conditions but which undergoes mass polymerization only when exposed to suitable actinic radiation, and where the photoacid generator utilized is completely miscible in the composition.

It is further an object of this invention to provide single component composition that can be used in a variety of other applications including for example 3D printing, ink-jettable coatings, sealants, and the like.

Other objects and further scope of the applicability of the present invention will become apparent from the detailed description that follows.

SUMMARY OF THE INVENTION

Surprisingly, it has now been found that by employing a single component composition, where a photoacid generator is completely miscible in the composition and thereby it is now possible to fabricate a variety of devices including for example an OLED device having a transparent optical layer which features hitherto unachievable properties, i.e., refractive index in the range of 1.4 to 1.6 or higher, high colorless optical transparency, desirable film thickness of the filler layer typically in the range of 10 to 20 µm but can be tailored to lower or higher film thickness depending upon the intended application, compatible with the OLED stack, particularly the cathode layer (a very thin layer on the top of the OLED stack), compatible with polymerization of the formulation on the OLED stack, including fast polymerization time and can be photolytically treated at ambient fabrication conditions, adhesion to both OLED stack and glass cover, and the like. It is also important to note that the compositions of this invention are expected to exhibit good uniform leveling across the OLED layer which typically requires a low viscosity. Further, compositions of this invention are also expected to exhibit low shrinkage due to their rigid polycycloolefinic structure. In addition, as the components of this invention undergo fast mass polymerization upon application they do not leave behind any fugitive small molecules which can damage the OLED stack. Generally, no other small molecule additives need to be employed thus offering additional advantages. Most importantly, the compositions of this invention are stable (i.e., no change in viscosity) at ambient atmospheric conditions including up to 40° C. for several days to weeks and undergo mass polymerization only when exposed to suitable actinic radiation. The compositions undergo mass vinyl addition polymerization very quickly when subjected to such actinic radiation and generally the compositions become solid objects in few minutes, i.e., within 1-10 minutes and more generally in less than one hour.

Advantageously, the compositions of this invention are also compatible with a "one drop fill" (commonly known as "ODF"). In a typical ODF process, which is commonly used to fabricate a top emission OLED device, a special optical fluid is applied to enhance the transmission of light from the device to the top cover glass, and the fluid is dispensed by an ODF method. Although the method is known as ODF which can be misleading because several drops or lines of material are generally dispensed inside the seal lines. After applying the fluid, the fluid spreads out as the top glass is laminated, analogous to die-attach epoxy. This process is generally carried out under vacuum to prevent air entrapment. The present invention allows for a material of low viscosity which readily and uniformly coats the substrate with rapid flow in a short period of time. Even more advantageously, the present invention overcomes the deficiencies faced by the prior art in that a single component composition is much more convenient than employing a two component system especially in an ODF method.

Accordingly, there is provided a single component composition encompassing a) a soluble photoacid generator of formula (I) or (II); b) an organopalladium compound of formula (III), an organopalladium compound of formula (IIIA) or an organopalladium compound of formula (IIIB) as described herein; c) one or more olefinic monomers of formula (V); and d) a photosensitizer.

In another aspect of this invention there is also provided a kit encompassing the composition of this invention for forming a three dimensional object, such as for example, a transparent film.

DETAILED DESCRIPTION

The terms as used herein have the following meanings:

As used herein, the articles "a," "an," and "the" include plural referents unless otherwise expressly and unequivocally limited to one referent.

Since all numbers, values and/or expressions referring to quantities of ingredients, reaction conditions, etc., used herein and in the claims appended hereto, are subject to the various uncertainties of measurement encountered in obtaining such values, unless otherwise indicated, all are to be understood as modified in all instances by the term "about."

Where a numerical range is disclosed herein such range is continuous, inclusive of both the minimum and maximum values of the range as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all sub-ranges subsumed therein. For example, a stated range of from "1 to 10" should be considered to include any and all sub-ranges between the minimum value of 1 and the maximum value of 10. Exemplary sub-ranges of the range 1 to 10 include, but are not limited to, 1 to 6.1, 3.5 to 7.8, and 5.5 to 10, etc.

As used herein, the symbol "⁓" denotes a position at which the bonding takes place with another repeat unit or another atom or molecule or group or moiety as appropriate with the structure of the group as shown.

As used herein, "hydrocarbyl" refers to a group that contains carbon and hydrogen atoms, non-limiting examples being alkyl, cycloalkyl, aryl, aralkyl, alkaryl, and alkenyl. The term "halohydrocarbyl" refers to a hydrocarbyl group where at least one hydrogen has been replaced by a halogen. The term perhalocarbyl refers to a hydrocarbyl group where all hydrogens have been replaced by a halogen.

As used herein, the expression "$(C_1-C_6)$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$(C_1-C_4)$alkoxy", "$(C_1-C_4)$thioalkyl" "$(C_1-C_4)$alkoxy$(C_1-C_4)$alkyl", "hydroxy$(C_1-C_4)$alkyl", "$(C_1-C_4)$alkylcarbonyl", "$(C_1-C_4)$alkoxycarbonyl$(C_1-C_4)$alkyl", "$(C_1-C_4)$alkoxycarbonyl", "diphenyl$(C_1-C_4)$alkyl", "phenyl$(C_1-C_4)$alkyl", "phenylcarboxy$(C_1-C_4)$alkyl" and "phenoxy$(C_1-C_4)$alkyl" are to be construed accordingly.

As used herein, the expression "cycloalkyl" includes all of the known cyclic groups. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly. It should further be noted that certain of the alkyl groups as described herein, such as for example, "$(C_1-C_6)$alkyl" may partially be fluorinated, that is, only portions of the hydrogen atoms in said alkyl group are replaced with fluorine atoms and shall be construed accordingly.

As used herein, the expression "$(C_6-C_{10})$aryl" means substituted or =substituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art.

As used herein, the expression "$(C_6-C_{10})$aryl$(C_1-C_4)$alkyl" means that the $(C_6-C_{10})$aryl as defined herein is further attached to $(C_1-C_4)$alkyl as defined herein. Representative examples include benzyl, phenylethyl, 2-phenylpropyl, 1-naphthylmethyl, 2-naphthylmethyl and the like.

"Halogen" or "halo" means chloro, fluoro, bromo, and iodo.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_6)$alkyl, $(C_2-C_6)$alkenyl, $(C_1-C_6)$perfluoroalkyl, phenyl, hydroxy, —$CO_2H$, an ester, an amide, $(C_1-C_6)$ alkoxy, $(C_1-C_6)$thioalkyl and $(C_1-C_6)$perfluoroalkoxy. However, any of the other suitable substituents known to one skilled in the art can also be used in these embodiments.

It should be noted that any atom with unsatisfied valences in the text, schemes, examples and tables herein is assumed to have the appropriate number of hydrogen atom(s) to satisfy such valences.

By the term "derived" is meant that the polymeric repeating units are polymerized (formed) from, for example, polycyclic norbornene-type monomers in accordance with formulae (I) to (IV) wherein the resulting polymers are formed by 2,3 enchainment of norbornene-type monomers as shown below:

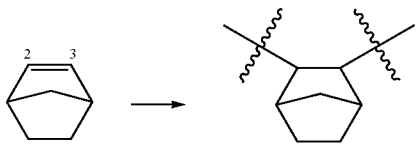

Accordingly, in accordance with the practice of this invention there is provided a single component composition encompassing a) a soluble photoacid generator selected from the group consisting of a compound of formula (I):

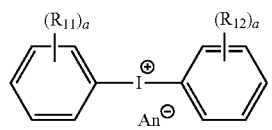

and a compound of formula (II):

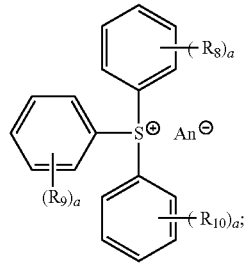

wherein:

a is an integer from 1 to 5;

$An^{\ominus}$ is selected from the group consisting of $Cl^{\ominus}$, $Br^{\ominus}$, $I^{\ominus}$, $BF_4^{\ominus}$, tetrakis(pentafluorophenyl)borate, tetrakis(3,5-bis(trifluoromethyl)phenyl)borate, tetrakis(2-fluorophenyl)borate, tetrakis(3-fluorophenyl)borate, tetrakis(4-fluorophenyl)borate, tetrakis(3,5-difluorophenyl)borate, tetrakis(2,3,4,5-tetrafluorophenyl)borate, tetrakis(3,4,5,6-tetrafluorophenyl)borate, tetrakis(3,4,5-trifluorophenyl)borate, methyltris(perfluorophenyl)borate, ethyltris(perfluorophenyl)borate, phenyltris(perfluorophenyl)borate, tetrakis(1,2,2-trifluoroethylenyl)borate, tetrakis(4-tri-1-propylsilyltetrafluorophenyl)borate, tetrakis(4-dimethyl-tert-butylsilyltetrafluorophenyl)borate, (triphenylsiloxy)tris(pentafluorophenyl)borate, (octyloxy)tris(pentafluorophenyl)borate, tetrakis[3,5-bis[1-methoxy-2,2,2-trifluoro-1-(trifluoromethyl)ethyl]pheny-l]borate, tetrakis[3-[1-methoxy-2,2,2-trifluoro-1-(trifluoromethyl)ethyl]-5-(trifluoromethyl)phenyl]borate, and tetrakis[3-[2,2,2-trifluoro-1-(2,2,2-trifluoroethoxy)-1-(trifluoromethyl)-ethyl]-5-(trifluoromethyl)phenyl]borate, tris(trifluoromethanesulfonyl)methide, bis(trifluoromethanesulfonyl)imide, $PF_6^{\ominus}$, $SbF_6^{\ominus}$, $n\text{-}C_4F_9SO_3^{\ominus}$, $CF_3SO_3^{\ominus}$ and $p\text{-}CH_3(C_6H_4)\text{—}SO_3^{\ominus}$;

at least one of $R_8$, $R_9$, $R_{10}$, $R_{11}$ and $R_{12}$ is selected from the group consisting of linear or branched $(C_{10}-C_{20})$alkyl, $(C_6-C_{10})$aryl$(C_{10}-C_{20})$alkyl, $(C_{10}-C_{20})$alkoxy, $(C_6-C_{10})$aryloxy$(C_{10}-C_{20})$alkyl, $(C_{10}-C_{20})$alkanoyl$(C_6-C_{10})$aryl and $(C_{10}-C_{20})$alkoxy$(C_6-C_{10})$aroyl$(C_6-C_{20})$alkyl; and the remaining $R_8$, $R_9$, $R_{10}$, $R_{11}$ and $R_{12}$ are the same or different and each independently selected from the group consisting of halogen, methyl, ethyl, linear or branched $(C_3-C_{20})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$ alkyl, $(C_6-C_{10})$-aryloxy, $(C_6-C_{10})$thioaryl, $(C_1-C_6)$alkanoyl $(C_6-C_{10})$thioaryl, $(C_1-C_6)$alkoxy$(C_6-C_{10})$aroyl$(C_1-C_6)$alkyl and $(C_6-C_{10})$thioaryl-$(C_6-C_{10})$diarylsulfonium salt;

b) an organopalladium compound selected from the group consisting of a compound of formula (III), a compound of formula (IIIA) and a compound of formula (IIIB):

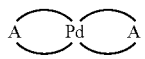

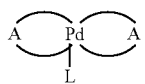

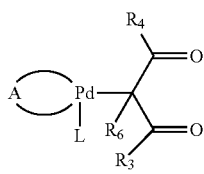

wherein:

L is a ligand selected from the group consisting of $P(R)_3$, $P(OR)_3$, $O=P(R)_3$, RCN and substituted or unsubstituted pyridines, where R is selected from the group consisting of methyl, ethyl, linear or branched $(C_3-C_{16})$alkyl, $(C_1-C_{16})$ perfluoroalkyl, $(C_3-C_{10})$cycloalkyl, $(C_6-C_{10})$aryl$(C_1-C_{16})$alkyl and substituted or unsubstituted $(C_6-C_{10})$aryl;

each A independently is a bidentate monoanionic ligand of formula (IV):

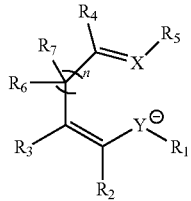

(IV)

wherein:

n is an integer 0, 1 or 2;

X and Y are independently of each other selected from O, N and S;

$R_1$, $R_2$, $R_3$, $R_4$, $R_5$, $R_6$ and $R_7$ are the same or different and each independently selected from the group consisting of hydrogen, methyl, ethyl, linear or branched $(C_3-C_{16})$alkyl, $(C_1-C_{16})$perfluoroalkyl, $(C_3-C_{10})$cycloalkyl, $(C_6-C_{10})$aryl $(C_1-C_{16})$alkyl and substituted or unsubstituted $(C_6-C_{10})$aryl; provided when either X or Y is O or S, $R_1$ and $R_5$, respectively, do not exist;

c) one or more olefinic monomers of the formula (V):

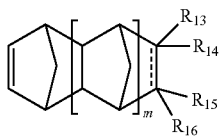

(V)

wherein:

m is an integer 0, 1 or 2;

≈≈≈≈ is a single bond or a double bond;

at least one of $R_{13}$, $R_{14}$, $R_{15}$ and $R_{16}$ is selected from the group consisting of linear or branched $(C_6-C_{16})$alkyl, $(C_6-C_{12})$aryl$(C_1-C_{16})$alkyl, $(C_6-C_{10})$aryloxy$(C_2-C_{16})$alkyl and $(C_6-C_{10})$aryl$(C_6-C_{10})$aryloxy$(C_1-C_{16})$alkyl;

the remaining $R_{13}$, $R_{14}$, $R_{15}$ and $R_{16}$ are the same or different and each independently selected from the group consisting of hydrogen, halogen, a hydrocarbyl or halohydrocarbyl group selected from methyl, ethyl, linear or branched $(C_3-C_{16})$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_6)$alkyl, methoxy, ethoxy, linear or branched $(C_3-C_{16})$alkoxy, perfluoro$(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy, $(C_6-C_{10})$aryl$(C_1-C_6)$alkoxy, perfluoro$(C_6-C_{10})$aryloxy, perfluoro$(C_6-C_{10})$aryl$(C_1-C_3)$alkoxy, a group of formula (A):

—Z-Aryl  (A);

a group of formula (A1):

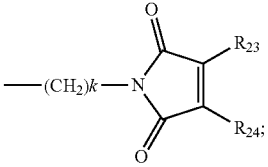

(A1)

a group of formula (A2):

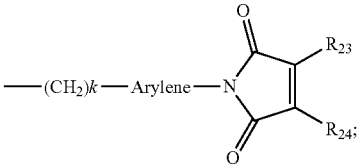

(A2)

a group of formula (A3):

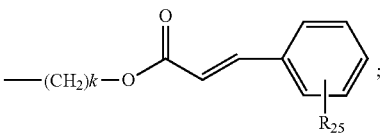

(A3)

and a group of formula (A4):

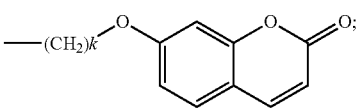

(A4)

wherein:

Z is selected from the group consisting of:
O, CO, C(O)O, OC(O), OC(O)O, S, $(CR_{17}R_{18})_b$, $O(CR_{17}R_{18})_b$, $(CR_{17}R_{18})_bO$, $C(O)(CR_{17}R_{18})_b$, $(CR_{17}R_{18})_bC(O)$, $C(O)O(CR_{17}R_{18})_b$, $(CR_{17}R_{18})_bC(O)O$, $OC(O)(CR_{17}R_{18})_b$, $(CR_{17}R_{18})_bOC(O)$, $(CR_{17}R_{18})_bOC(O)O$, $(CR_{17}R_{18})_bOC(O)O(CR_{17}R_{18})_b$, $OC(O)O(CR_{17}R_{18})_b$, $S(CR_{17}R_{18})_b$, $(CR_{17}R_{18})_bS$, $(SiR_{17}R_{18})_b$, $O(SiR_{17}R_{18})_b$, $(SiR_{17}R_{18})_bO$, where $R_{17}$ and $R_{18}$ are the same or different and each independently selected from hydrogen, methyl, ethyl, linear or branched $(C_3-C_{12})$alkyl, substituted or unsubstituted $(C_6-C_{14})$aryl, methoxy, ethoxy, linear or branched $(C_3-C_6)$alkyloxy, $(C_2-C_6)$acyl, $(C_2-C_6)$acyloxy, and substituted or unsubstituted $(C_6-C_{14})$aryloxy; and b is an integer from 0 to 12, inclusive;

Aryl is selected from the group consisting of substituted or unsubstituted phenyl, substituted or unsubstituted biphenyl and substituted or unsubstituted naphthyl, substituted or unsubstituted terphenyl, substituted or unsubstituted anthracenyl substituted or unsubstituted fluorenyl, wherein said substituents are selected from the group consisting of halogen, methyl, ethyl, linear or branched $(C_3-C_6)$alkyl, perfluoro($C_1$-$C_{12}$)alkyl, ($C_3$-$C_{12}$)cycloalkyl, ($C_6$-$C_{10}$)aryl, ($C_6$-$C_{10}$)aryl($C_1$-$C_6$)alkyl, perfluoro($C_6$-$C_{10}$)aryl, perfluoro($C_6$-$C_{10}$)aryl($C_1$-$C_6$)alkyl, methoxy, ethoxy, linear or branched ($C_3$-$C_{16}$)alkoxy, perfluoro($C_1$-$C_{12}$)alkoxy, ($C_3$-$C_{12}$)cycloalkoxy, ($C_6$-$C_{10}$)aryloxy, ($C_6$-$C_{10}$)aryl($C_1$-$C_6$)alkoxy, perfluoro($C_6$-$C_{10}$)aryloxy and perfluoro($C_6$-$C_{10}$)aryl($C_1$-$C_3$)alkoxy;

k is an integer from 1 to 12;

$R_{23}$, $R_{24}$ and $R_{25}$ are the same or different and each independently selected from the group consisting of hydrogen, methyl, ethyl, linear or branched ($C_3$-$C_{12}$)alkyl, perfluoro($C_1$-$C_{12}$)alkyl, methoxy, ethoxy, linear or branched ($C_3$-$C_{12}$)alkoxy, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_6$)alkyl, perfluoro($C_6$-$C_{10}$)aryl and perfluoro($C_6$-$C_{10}$)aryl($C_1$-$C_6$)alkyl; or $R_{23}$ and $R_{24}$ taken together with the intervening carbon atoms to which they are attached to form a substituted or unsubstituted ($C_5$-$C_{14}$)cyclic, ($C_5$-$C_{14}$)bicyclic or ($C_5$-$C_{14}$) tricyclic ring; and Arylene is substituted or unsubstituted bivalent ($C_6$-$C_{14}$)aryl;

or one of $R_1$ and $R_2$ taken together with one of $R_3$ and $R_4$ and the carbon atoms to which they are attached to form a substituted or unsubstituted ($C_5$-$C_{14}$)cyclic, ($C_5$-$C_{14}$)bicyclic or ($C_5$-$C_{14}$)tricyclic ring;

and a) a photosensitizer.

More specifically, the Aryl as defined herein is substituted or unsubstituted biphenyl of formula:

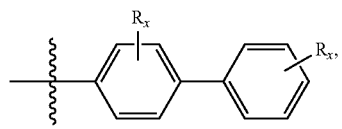
b)

c) substituted or unsubstituted naphthyl of formula:

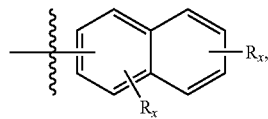
d)

e) substituted or unsubstituted terphenyl of formula:

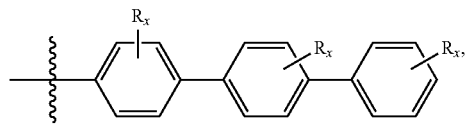
f)

g) substituted or unsubstituted anthracenyl of formula:

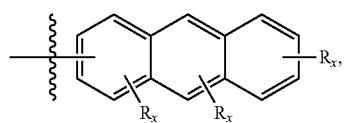
h)

i) substituted or unsubstituted fluorenyl of formula:

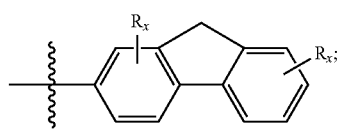
j)

k) where $R_x$ in each occurrence is independently selected from methyl, ethyl, linear or branched ($C_3$-$C_{12}$)alkyl or ($C_6$-$C_{10}$)aryl.

It should be noted that the ligand, L of the organopalladium compounds of formulae (IIIA) or (IIIB) can generally be a Lewis Base, which is coordinately bonded to palladium. That is, the Lewis Base is bonded to palladium by sharing both of its lone pair of electrons. Accordingly, any of the Lewis Base known in the art can be used for this purpose. Advantageously, it has now been found that a Lewis Base, which can dissociate readily under the polymerization conditions as described further in detail below generally provides more suitable compounds of formula (IIIA) or (IIIB) as polymerization catalysts, i.e., initiators. Thus, in one aspect of this invention judicious selection of the Lewis Base (LB) will provide a modulation of the catalytic activity of the compounds of this invention.

Accordingly, it has now been found that suitable LBs that can be employed include without any limitation substituted and unsubstituted nitriles, including alkyl nitrile, aryl nitrile or aralkyl nitrile; phosphine oxides, including substituted and unsubstituted trialkyl phosphine oxides, triaryl phosphine oxides, triarylalkyl phosphine oxides, and various combinations of alkyl, aryl and aralkyl phosphine oxides; substituted and unsubstituted pyrazines; substituted and unsubstituted pyridines; phosphites, including substituted and unsubstituted trialkyl phosphites, triaryl phosphites, triarylalkyl phosphites, and various combinations of alkyl, aryl and aralkyl phosphites; phosphines, including substituted and unsubstituted trialkyl phosphines, triaryl phosphines, triarylalkyl phosphines, and various combinations of alkyl, aryl and aralkyl phosphines. Various other LBs that may be employed include various ethers, alcohols, ketones, amines and anilines, arsines, stibines, and the like.

1) In some embodiments of this invention, the LB is selected from acetonitrile, propionitrile, n-butyronitrile, tert-butyronitrile, benzonitrile ($C_6H_5CN$), 2,4,6-trimethylbezonitrile, phenyl acetonitrile ($C_6H_5CH_2CN$), pyridine, 2-methylpyridine, 3-methylpyridine, 4-methylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 2,6-di-t-butylpyridine, 2,4-di-t-butylpyridine, 2-methoxypyridine, 3-methoxypyridine, 4-methoxypyridine, pyrazine, 2,3,5,6-tetramethylpyrazine, diethyl ether, di-n-butyl ether, dibenzyl ether, tetrahydrofuran, tetrahydropyran, benzophenone, triphenylphosphine oxide, triphenyl phosphate or phosphines or phosphites of formula $PR_3$, where R is independently selected from methyl, ethyl, ($C_3$-$C_6$)alkyl, substituted or unsubstituted ($C_3$-$C_7$)cycloalkyl, ($C_6$-$C_{10}$)aryl, ($C_6$-$C_{10}$)aralkyl, methoxy, ethoxy, ($C_3$-$C_6$)alkoxy, substituted or unsubstituted ($C_3$-$C_7$)cycloalkoxy, ($C_6$-$C_{10}$)aryloxy or ($C_6$-$C_{10}$)arylalkoxy. Representative examples of $PR_3$ include without any limitation trimethyl phosphine, triethyl phosphine, tri-n-propyl phosphine, tri-iso-propyl phosphine, tri-n-butyl phosphine, tri-iso-butyl phosphine, tri-tert-butyl phosphine, tricyclopentylphosphine, triallylphosphine, tricyclohexylphosphine, triphenyl phosphine, trimethyl phosphite, triethyl phosphite, trifluoroethyl phosphite, tri-n-propyl phosphite, tri-iso-propyl phosphite, tri-n-butyl phosphite, tri-iso-butyl phosphite, tri-tert-butyl phosphite, tricyclopentyiphosphite, triallylphosphite, tricyclohexylphosphite, triphenyl phosphite, and the like. It should however be noted that various other known LBs which will bring about the intended activity can also be used in this embodiment of the invention.

Various olefinic monomers which undergo vinyl addition polymerization can be employed in the composition of this invention. Such olefinic monomers include without any limitation alicyclic olefins, such as ethylene, propylene, butylene, styrene, and the like. Other olefinic monomers include cyclo-olefins and bicyclo-olefins, and so on.

In some embodiments of this invention the olefinic monomers which are suitable in the composition of this invention are of the formula (V), wherein:
m=0 or 1;
----- is a single bond;
at least one of $R_{13}$, $R_{14}$, $R_{15}$ and $R_{16}$ is selected from the group consisting of n-hexyl, n-heptyl, n-octyl, n-nonyl, n-decyl, n-dodecyl, phenylbutyl, phenoxyethyl, biphenyloxyethyl and biphenyloxybutyl.

The monomers of formula (V) as described herein are themselves known in the literature or can be prepared by any of the known methods in the art to make such or similar types of monomers.

In addition, the monomers as described herein readily undergo mass vinyl addition polymerization, i.e., in their neat form without use of any solvents by vinyl addition polymerization using transition metal procatalysts, such as for example, organopalladium compounds as described herein. See for example, U.S. Pat. Nos. 7,442,800 B2; and 7,759,439 B2; pertinent portions of which are incorporated herein by reference. The term "mass polymerization" as used herein shall have the generally accepted meaning in the art. That is, a polymerization reaction that is generally carried out substantially in the absence of a solvent. In some cases, however, a small proportion of solvent is present in the reaction medium. For example, such small amounts of solvent may be used to dissolve the organopalladium compound of formulae (III), (IIIA) or (IIIB), and a photoacid generator or photosensitizer as described herein or convey the same to the reaction medium. Also, some solvent may be used to reduce the viscosity of the monomer. The amount of solvent that can be used in the reaction medium may be in the range of 0 to 5 weight percent based on the total weight of the monomers employed. Any of the suitable solvents that dissolves the organopalladium compound of formulae (III), (IIIA) or (IIIB), a photoacid generator or photosensitizer and/or monomers can be employed in this invention. Examples of such solvents include alkanes, cycloalkanes, aromatics, such as toluene, ester solvents such as ethyl acetate, THF, dichloromethane, dichloroethane, and the like.

Advantageously, it has now been found that one or more of the monomers themselves can be used to dissolve the organopalladium compound of formulae (III), (IIIA) or (IIIB) or a photoacid generator or photosensitizer and thus avoiding the need for the use of solvents. In addition, one monomer can itself serve as a solvent for the other monomer and thus eliminating the need for an additional solvent. For example, if a first monomer of formula (V) is a solid at room temperature, then a second monomer of formula (V), which is a liquid at room temperature can be used as a solvent for the first monomer of formula (V) which is a solid or vice versa. Therefore, in such situations more than one monomer can be employed in the composition of this invention.

In some embodiments, the monomers of formula (V) employed in the composition of this invention may serve as high refractive index materials imparting high refractive index to the resulting polymeric film upon mass polymerization. In general, the monomers of formula (V) which are suitable in this invention feature a refractive index of at least 1.5. In some embodiments the refractive index of the monomers of formula (V) is higher than 1.5. In some other embodiments the refractive index of the monomers of formula (V) is in the range from about 1.5 to 1.6. In yet some other embodiments the refractive index of the monomers of formula (V) is higher than 1.55, higher than 1.6 or higher than 1.65. In some other embodiments it may even be higher than 1.7.

In some other embodiments, it is generally contemplated that monomer of formula (V) may also be used as a viscosity modifier. Accordingly, in general, such a monomer of formula (V) is a liquid at room temperature and can be used in conjunction with another monomer of formula (V) which is a solid or a high viscosity liquid.

In a further embodiment of this invention the composition of this invention encompasses at least two different monomers of formula (V) and is in a clear liquid state having a viscosity below 100 centipoise. In general, the composition of this invention exhibits low viscosity, which can be below 100 centipoise. In some embodiments, the viscosity of the composition of this invention is less than 90 centipoise. In some other embodiments the viscosity of the composition of this invention is in the range from about 10 to 100 centipoise. In yet some other embodiments the viscosity of the composition of this invention is lower than 80 cP, lower than 60 cP, lower than 40 cP, lower than 20 cP. In some other embodiments it may even be lower than 20 cP.

When the composition of this invention contains two monomers, they can be present in any desirable amounts that would bring about the intended benefit, including either refractive index modification or viscosity modification or both or any other desirable property depending upon the intended final application. Accordingly, the molar ratio of first monomer of formula (V) to second monomer of formula (V) can be from 0:100 to 100:0. That is, only one monomer of formula (V) can be employed in certain applications. In other words, any amount of these two monomers can be employed. In some embodiments, the molar ratio of first monomer of formula (V):second monomer of formula (V) is in the range from 1:99 to 99:1; in some other embodiments it is from 5:95 to 95:5; it is from 10:90 to 90:10; it is from 20:80 to 80:20; it is from 30:70 to 70:30; it is from 60:40 to 40:60; and it is 50:50, and so on.

In general, the compositions in accordance with the present invention encompass the above described one or more of monomer of formula (V), as it will be seen below, various composition embodiments are selected to provide properties to such embodiments that are appropriate and desirable for the use for which such embodiments are directed, thus such embodiments are tailorable to a variety of specific applications. Accordingly, in some embodiments the composition of this invention contains more than two distinct monomers of formula (V), such as for example three different monomers of formula (V) or four different monomers of formula (V).

For example, as already discussed above, proper combination of different monomers of formula (V) makes it possible to tailor a composition having the desirable refractive index, viscosity and optical transmission properties, among other properties. In addition, it may be desirable to include other polymeric or monomeric materials which are compatible to provide desirable optical properties depending upon the end use application. Accordingly, the compositions of this invention can also include other high refractive polymeric materials which will bring about such intended benefit. Examples of such polymers include without any limitation, poly(α-methylstyrene), poly(vinyl-toluene), copolymers of α-methylstyrene and vinyl-toluene, and the like.

Advantageously, it has further been found that the compositions of this invention can also contain additional monomers different from the monomer of formula (V). In some embodiments, the composition according to this invention may further contain one or more monomers selected from monomer of formula (VI) or monomer of formula (VII).

The monomer of formula (VI) is:

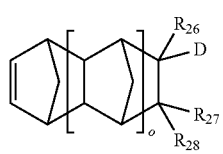
(VI)

wherein:
o is an integer from 0 to 2, inclusive;
D is $SiR_{29}R_{30}R_{31}$ or a group selected from:

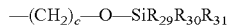 (E);

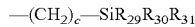 (F); and

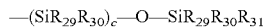 (G); wherein c is an integer from 1 to 10, inclusive, and where one or more of $CH_2$ is optionally substituted with $(C_1-C_{10})$alkyl or $(C_1-C_{10})$perfluoroalkyl;

$R_{26}$, $R_{27}$ and $R_{28}$ are the same or different and independently of each other selected from hydrogen, halogen and hydrocarbyl, where hydrocarbyl is selected from methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$alkyl or $(C_6-C_{10})$aryloxy; and $R_{29}$, $R_{30}$ and $R_{31}$ are each independently of one another methyl, ethyl, linear or branched $(C_3-C_9)$alkyl, substituted or unsubstituted $(C_6-C_{14})$aryl, methoxy ethoxy, linear or branched $(C_3-C_9)$alkoxy or substituted or unsubstituted $(C_6-C_{14})$aryloxy.

In this aspect of the invention, it has now been found that monomers of formula (VI) provides further advantages. Namely, the monomers of formula (VI) depending upon the nature of the monomer may impart high or low refractive index to the composition, thus it can be tailored to meet the need. In addition, the monomers of formula (VI) generally improve the adhesion properties and thus can be used as "adhesion modifiers." Finally, the monomers of formula (VI) may exhibit low viscosity and good solubility for the procatalyst and/or activator, among various other advantages.

The monomer of formula (VII) is:

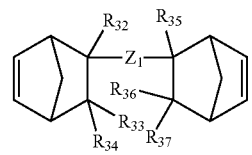
(VII)

wherein:

$Z_1$ is selected from the group consisting of substituted or unsubstituted $(C_1-C_{12})$alkylene, $-(CH_2)_dO(CH_2)_e-$, $-(CH_2)_d(SiR_{38}R_{39})(OSiR_{40}R_{41})_f(CH_2)_e-$ where d, e and f are independently integers from 0 to 6, inclusive, $R_{38}$, $R_{39}$, $R_{40}$ and $R_{41}$ are the same or different and independently of each other selected from methyl, ethyl, linear or branched $(C_3-C_{12})$alkyl, and an arylene selected from the following:

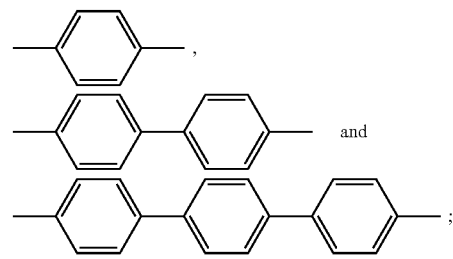

$R_{32}$, $R_{33}$, $R_{34}$, $R_{35}$, $R_{36}$ and $R_{37}$ are the same or different and independently of each other selected from hydrogen, halogen and hydrocarbyl, where hydrocarbyl is selected from methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$alkyl or $(C_6-C_{10})$-aryloxy.

The monomers of formula (VII) are bifunctional monomers and may exhibit high refractive index especially when $Z_1$ is an arylene group. Accordingly, it is contemplated that incorporation of monomers of formula (VII) into composition of this invention generally increases the refractive index of the composition and also increase crosslinkability with other molecules. Thus, by incorporation of monomers of formula (VII) into the composition of this invention it may be possible to increase compatibility with other materials depending upon the intended application thereby enhancing the properties of the composition of the invention.

In another aspect of this invention it is conceivable that the composition of this invention may contain only one monomer of formula (V) or formula (VI) or formula (VII). That is, any one of the monomers of formulae (V) to (VII) may be sufficient to form a composition of this invention. In some other embodiments the composition of this invention encompasses any two monomers of formulae (V) to (VII) and in any desirable proportions. In some other embodiments the composition of this invention encompasses any three monomers of formulae (V) to (VII) in any combinations thereof and in any desirable proportions. All such possible permutations and combinations of monomers of formulae (V) to (VII) are part of this invention.

Accordingly, any of the monomers within the scope of monomer of formula (V) can be employed in the composition of the invention. Representative examples of monomer of formula (V) include the following without any limitations:

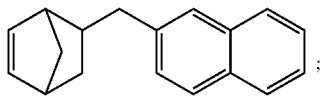

2-(bicyclo[2.2.1]hept-5-en-2-ylmethyl)naphthalene

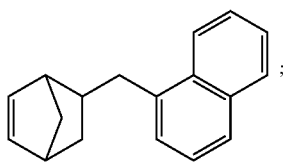

1-(bicyclo[2.2.1]hept-5-en-2-ylmethyl)naphthalene

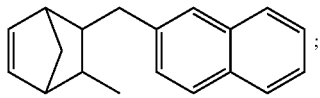

2-((3-methylbicyclo[2.2.1]hept-5-en-2-yl)methyl)naphthalene

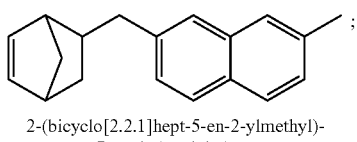

2-(bicyclo[2.2.1]hept-5-en-2-ylmethyl)-7-methylnaphthalene

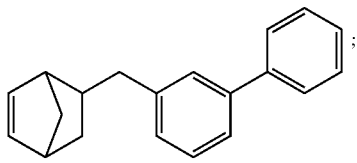

5-([1,1'-biphenyl]-3-ylmethyl)bicyclo[2.2.1]hept-2-ene

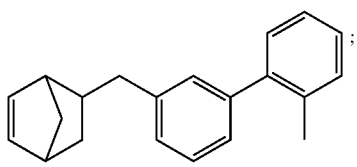

5-((2'-methyl-[1,1'-biphenyl]-3-yl)methyl)bicyclo[2.2.1]hept-2-ene

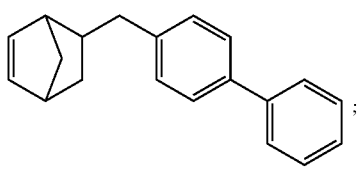

5-([1,1'-biphenyl]-4-ylmethyl)bicyclo[2.2.1]hept-2-ene

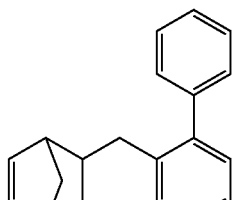

5-([1,1'-biphenyl]-2-ylmethyl)bicyclo[2.2.1]hept-2-ene

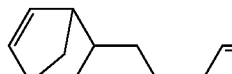

5-(2-([1,1'-biphenyl]-4-yl)ethyl)bicyclo[2.2.1]hept-2-ene (NBEtPhPh)

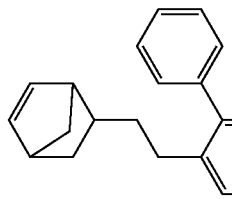

5-(2-([1,1'-biphenyl]-2-yl)ethyl)bicyclo[2.2.1]hept-2-ene

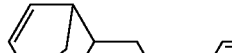

5-(2-(4'-ethyl-[1,1'-biphenyl]-4-yl)ethyl)bicyclo[2.2.1]hept-2-ene

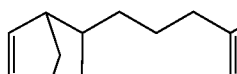

5-(3-([1,1'-biphenyl]-4-yl)propyl)bicyclo[2.2.1]hept-2-ene

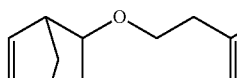

5-(2-([1,1'-biphenyl]-4-yl)ethoxy)bicyclo[2.2.1]hept-2-ene

5-(2-(2',4'-dimethyl-[1,1'-biphenyl]-4-yl)ethoxy)bicyclo[2.2.1]hept-2-ene

-continued

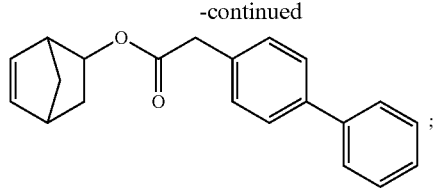

bicyclo[2.2.1]hept-5-en-2-yl 2-
([1,1'-biphenyl]-4-yl)acetate

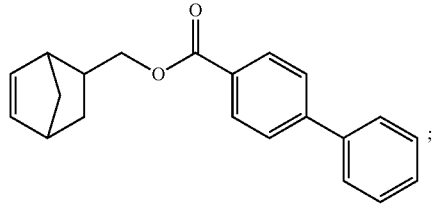

bicyclo[2.2.1]hept-5-en-2-ylmethyl
[1,1'-biphenyl]-4-carboxylate

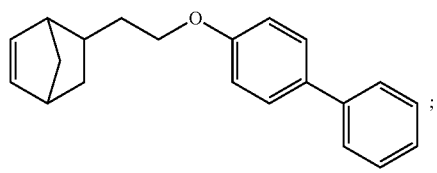

5-(2-([1,1'-biphenyl]-4-yloxy)ethyl)
bicyclo[2.2.1]hept-2-ene

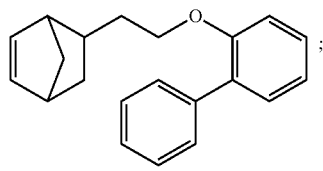

5-(2-([1,1'-biphenyl]-2-yloxy)ethyl)
bicyclo[2.2.1]hept-2-ene (NBEtOPhPh)

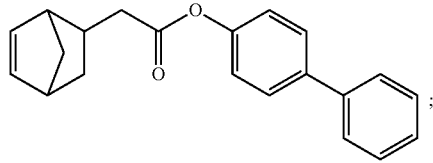

[1,1'-biphenyl]-4-yl 2-(bicyclo
[2.2.1]hept-5-en-2-yl)acetate

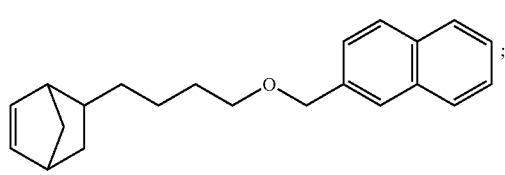

2-((4-(bicyclo[2.2.1]hept-5-en-2-yl)butoxy)methyl)naphthalene

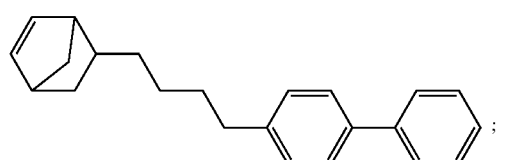

5-(4-([1,1'-biphenyl]-4-yl)butyl)bicyclo[2.2.1]hept-2-ene

-continued

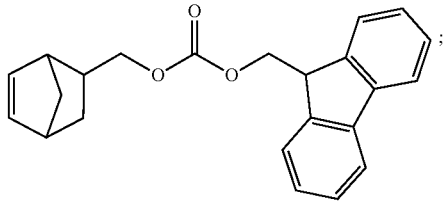

(9H-fluoren-9-yl)methyl (bicyclo[2.2.1]
hept-5-en-2-ylmethyl) carbonate

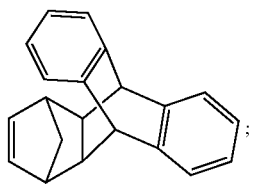

(9R,10S,11R,12S)-9,10-
dihydro-9,10-[2]
bicycloanthracene

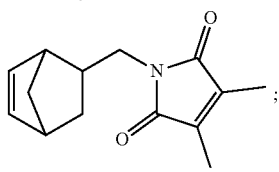

1-(4-bicyclo[2.2.1]hept-5-en-2-
ylmethyl)-3,4-dimethyl-1H-
pyrrole-2,5-dione (MeDMMINB)

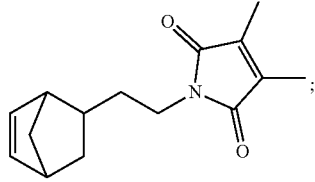

1-(4-bicyclo[2.2.1]hept-5-en-2-ylethyl)-
3,4-dimethyl-1H-pyrrole-2,5-dione
(EtDMMINB)

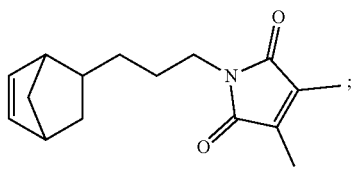

1-(4-bicyclo[2.2.1]hept-5-en-2-ylpropyl)-
3,4-dimethyl-1H-pyrrole-2,5-dione
(PrDMMINB)

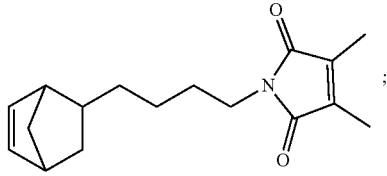

1-(4-bicyclo[2.2.1]hept-5-en-2-ylbutyl)-3,4-
dimethyl-1H-pyrrole-2,5-dione (BuDMMINB)

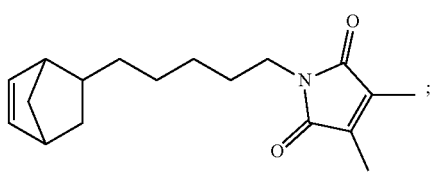

1-(4-bicyclo[2.2.1]hept-5-en-2-ylpentyl)-3,4-
dimethyl-1H-pyrrole-2,5-dione (PentylDMMINB)

-continued

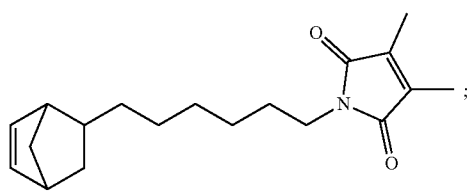

1-(4-bicyclo[2.2.1]hept-5-en-2-ylhexyl)-3,4-
dimethyl-1H-pyrrole-2,5-dione (HxDMMINB)

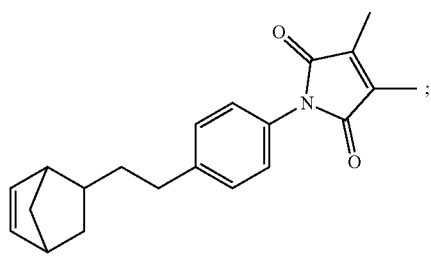

1-(4-bicyclo[2.2.1]hept-5-en-2-ylethyl)1,4-phenylene-
3,4-dimethyl-1H-pyrrole-2,5-dione (EtPhDMMINB)

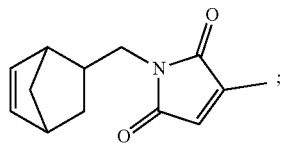

1-(4-bicyclo[2.2.1]hept-5-en-2-
ylmethyl)-3-methyl-1H-pyrrole-
2,5-dione (MeMMINB)

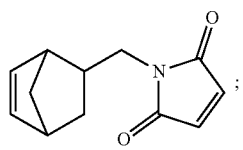

1-(4-bicyclo[2.2.1]
hept-5-en-2-ylmethyl)-
1H-pyrrole-2,5-dione
(MeMINB)

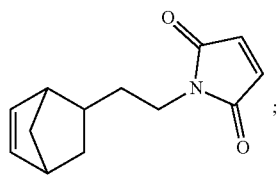

1-(4-bicyclo[2.2.1]hept-5-en-2-
ylethyl)-1H-pyrrole-2,5-dione
(EtMINB)

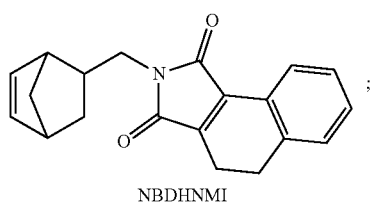

NBDHNMI

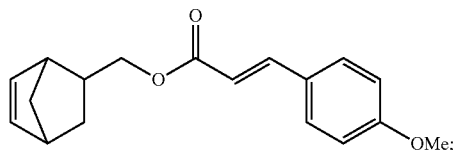

bicyclo[2.2.1]hept-5-en-2-ylmethyl 4-methoxy-cinnamate
(NBMeMeOCinn)

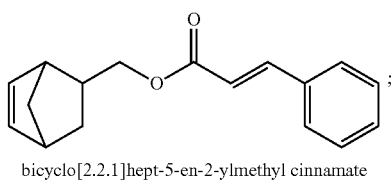

bicyclo[2.2.1]hept-5-en-2-ylmethyl cinnamate
(NBMeCinn)

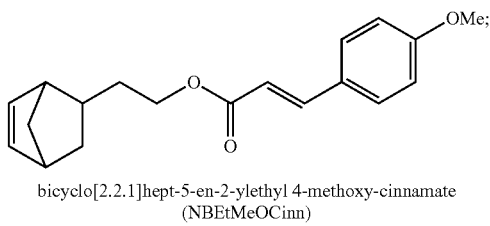

bicyclo[2.2.1]hept-5-en-2-ylethyl 4-methoxy-cinnamate
(NBEtMeOCinn)

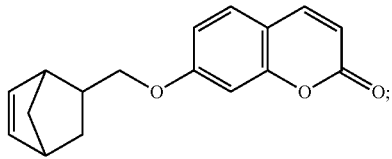

7-(bicyclo[2.2.1]hept-5-en-2-ylmethoxy)-
2H-chromen-2-one (NBMeCoum)

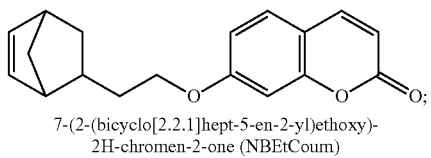

7-(2-(bicyclo[2.2.1]hept-5-en-2-yl)ethoxy)-
2H-chromen-2-one (NBEtCoum)

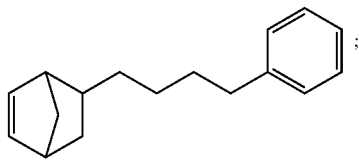

5-(4-phenylbutyl)bicyclo[2.2.1]hept-2-ene

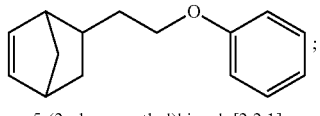

5-(2-phenoxyethyl)bicyclo[2.2.1]
hept-2-ene

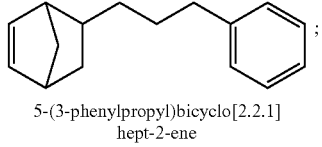

5-(3-phenylpropyl)bicyclo[2.2.1]
hept-2-ene

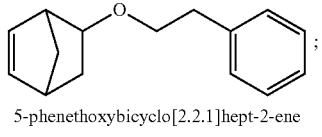

5-phenethoxybicyclo[2.2.1]hept-2-ene

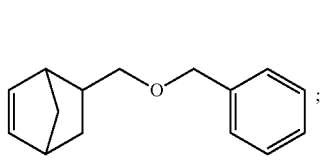

5-((benzyloxy)methyl)bicyclo[2.2.1]
hept-2-ene

-continued

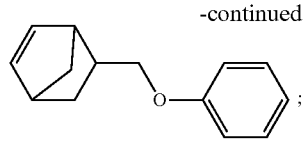

5-(phenoxymethyl)bicyclo[2.2.1]
hept-2-ene

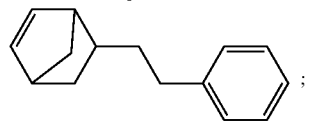

5-phenethylbicyclo[2.2.1]hept-2-ene
(PENB)

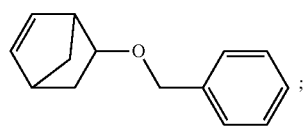

5-(benzyloxy)bicyclo[2.2.1]
hept-2-ene

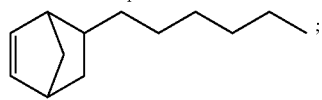

5-hexylbicyclo[2.2.1]hept-2-ene
(HexylNB)

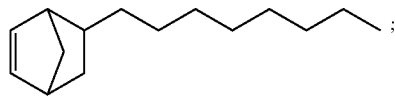

5-octylbicyclo[2.2.1]hept-2-ene (OctNB)

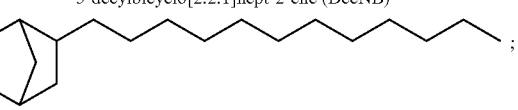

5-decylbicyclo[2.2.1]hept-2-ene (DecNB)

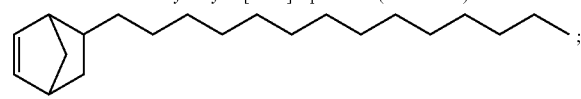

5-dodecylbicyclo[2.2.1]hept-2-ene (DoDecNB)

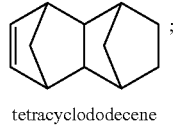

5-tetradecylbicyclo[2.2.1]hept-2-ene (TetraDecNB)

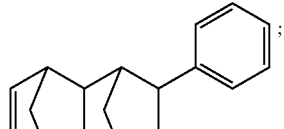

tetracyclododecene
(TD)

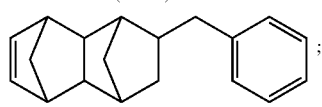

2-phenyl-tetracyclododecene
(PhTD)

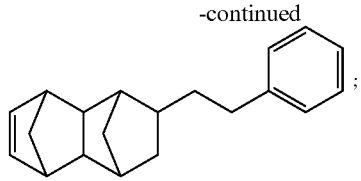

2-benzyl-1,2,3,4,4a,5,8,8a-octahydro-
1,4:5,8-dimethanonaphthalene

-continued

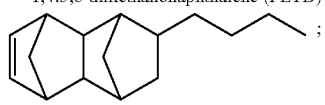

2-phenethyl-1,2,3,4,4a,5,8,8a-octahydro-
1,4:5,8-dimethanonaphthalene (PETD)

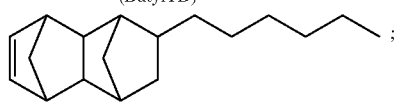

2-butyl-1,2,3,4,4a,5,8,8a-octahydro-
1,4:5,8-dimethanonaphthalene
(ButylTD)

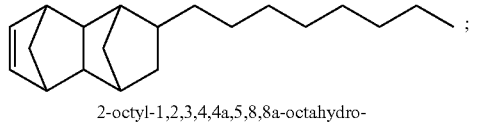

2-hexyl-1,2,3,4,4a,5,8,8a-octahydro-
1,4:5,8-dimethanonaphthalene (HexylTD)

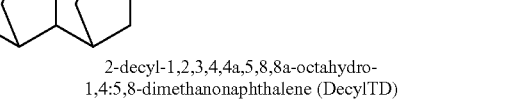

2-octyl-1,2,3,4,4a,5,8,8a-octahydro-
1,4:5,8-dimethanonaphthalene (OctylTD)

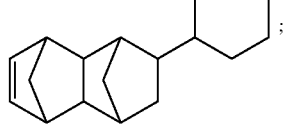

2-decyl-1,2,3,4,4a,5,8,8a-octahydro-
1,4:5,8-dimethanonaphthalene (DecylTD)

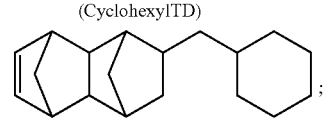

2-cyclohexyl-tetracyclododecene
(CyclohexylTD)

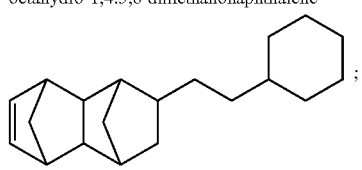

2-cyclohexylmethyl-1,2,3,4,4a,5,8,8a-
octahydro-1,4:5,8-dimethanonaphthalene

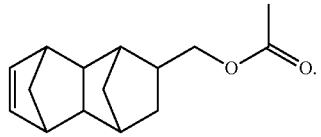

2-cyclohexylethyl-1,2,3,4,4a,5,8,8a-
octahydro-1,4:5,8-dimethanonaphthalene

; and (1,2,3,4,4a,5,8,8a-octahydro-1,4:5,8-
dimethanonaphthalen-2-yl)
methyl acetate (TDMeOAc)

Turning now to monomer of formula (VI) to form the composition of this invention it is contemplated that any monomer within the scope of monomer of formula (VI) can be employed. Exemplary monomers of such type include but not limited to those selected from the group consisting of

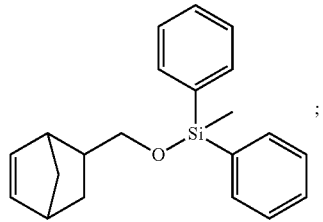

(bicyclo[2.2.1]hept-5-en-2-ylmethoxy)
(methyl)diphenylsilane
(NBCH$_2$OSiMePh$_2$)

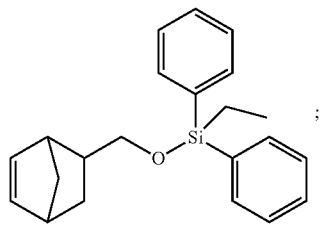

(bicyclo[2.2.1]hept-5-en-2-ylmethoxy)
(ethyl)diphenylsilane

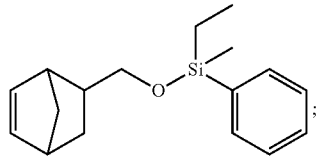

(bicyclo[2.2.1]hept-5-en-2-ylmethoxy)
(ethyl)(methyl)(phenyl)silane

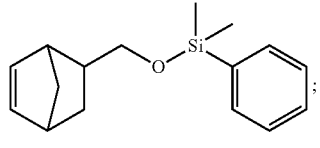

(bicyclo[2.2.1]hept-5-en-2-ylmethoxy)
dimethyl(phenyl)silane

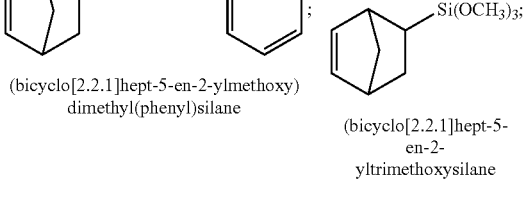

(bicyclo[2.2.1]hept-5-en-2-yltrimethoxysilane

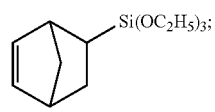

(bicyclo[2.2.1]hept-5-en-2-yltriethoxysilane
(TESNB, NBSi(OC$_2$H$_5$)$_3$)

(bicyclo[2.2.1]hept-5-en-2-yl(tert-butoxy)dimethoxysilane

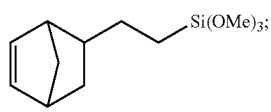

2-(bicyclo[2.2.1]hept-5-en-2-yl)ethyl)trimethoxysilane

-continued

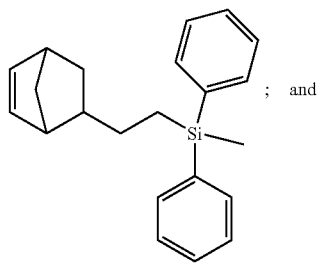  ; and (2-(bicyclo[2.2.1]hept-5-en-2-yl)ethyl)(methyl)diphenylsilane

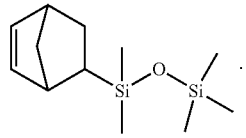

1-(bicyclo[2.2.1]hept-5-en-2-yl)-1,1,3,3,3-pentamethyldisiloxane

Turning now to monomer of formula (VII) to form the composition of this invention it is contemplated that any monomer within the scope of monomer of formula (VII) can be employed. Exemplary monomers of such type include but not limited to those selected from the group consisting of:

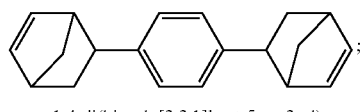

1,4-di(bicyclo[2.2.1]hept-5-en-2-yl)benzene

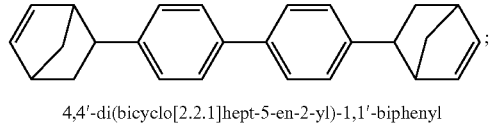

4,4'-di(bicyclo[2.2.1]hept-5-en-2-yl)-1,1'-biphenyl

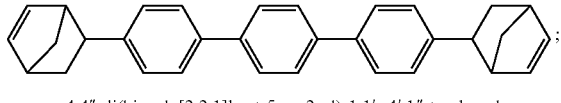

4,4''-di(bicyclo[2.2.1]hept-5-en-2-yl)-1,1':-4',1''-terphenyl

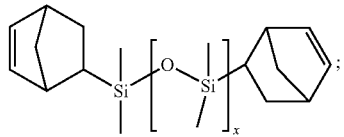

1,3-di(bicyclo[2.2.1]hept-5-en-2-yl)-1,1,3,3-tetramethyldisiloxane,
when x = 1 and 1,5-di(bicyclo[2.2.1]hept-5-en-2-yl)-1,1,3,3,5,5-hexamethyltrisiloxane,
when x = 2

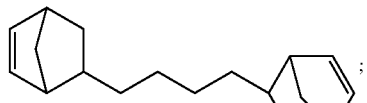

1,4-di(bicyclo[2.2.1]hept-5-en-2-yl)butane

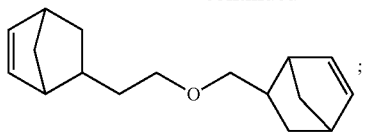

5,5'-(oxybis(ethane-2,1-diyl))bis
(bicyclo[2.2.1]hept-2-ene)

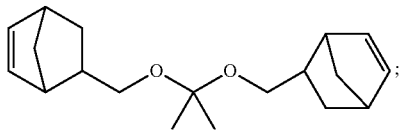

5,5'-((propane-2,2-diylbis(oxy))bis(methylene))
bis(bicyclo[2.2.1]hept-2-ene)

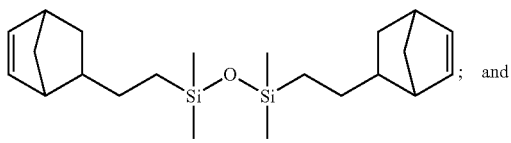; and 1,3-bis(norbornenylethyl)-1,1,3,3,-tetramethyldisiloxane
(BisNBEt-Disiloxane)

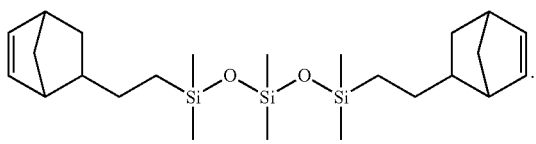

1,5-bis(norbornenylethyl)-1,1,3,3,5,5,-hexmethyltrisiloxane
(BisNBEt-Trisiloxane)

In a further embodiment, the composition of this invention encompasses one or more monomers of formula (V) and at least one monomer of formula (VI).

In another embodiment, the composition of this invention encompasses one or more monomers of formula (VI) and at least one monomer of formula (VII) and optionally one monomer of formula (V).

In yet a further embodiment, the composition of this invention encompasses at least one monomer of formula (V) and at least one monomer of formula (VI), and optionally one monomer of formula (VII).

In yet a further embodiment, the composition of this invention encompasses one monomer of formula (VI), optionally one or more monomers of formula (V) or monomer of formula (VII).

In yet another embodiment, the composition of this invention may include one or more monomers selected from the following:

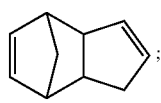

dicyclopentadiene
(DCPD)

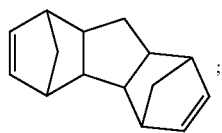

4,4a,4b,5,8,8a,9,9a-
octahydro-
1H-1,4:5,8-
dimethanofluorene
(one of trimers of
cyclopentadiene,
(TCPD2)

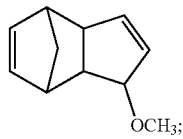

1-methoxy-
dicyclopentadiene

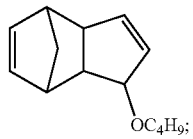

1-(n-butoxy)-
dicyclopentadiene

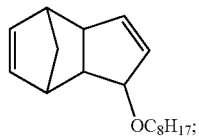

1-(n-octyloxy)-
dicyclopentadiene

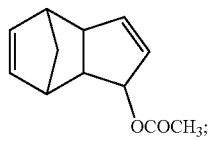

3a,4,7,7a-tetrahydro-
1H-4,7-methanoinden-
1-yl acetate

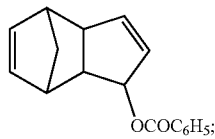

3a,4,7,7a-tetrahydro-
1H-4,7-methanoinden-
1-yl benzoate

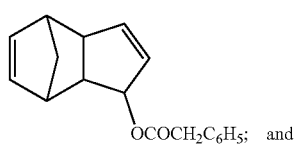; and 3a,4,7,7a-tetrahydro-
1H-4,7-methanoinden-
1-yl 2-phenylacetate -continued

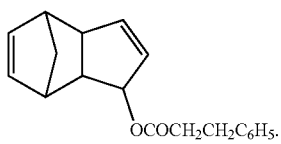

3a,4,7,7a-tetrahydro-
1H-4,7-methanoinden-
1-yl 3-phenylpropanoate

In a further embodiment of this invention, the composition contains any of the organopalladium compounds of formulae (III), (IIIA) or (IIIB) that would bring about the mass polymerization as described herein. Generally, such suitable organopalladium compounds of formulae (III), (IIIA) or (IIIB) contain a bidentate monoanionic ligand which is selected from the group consisting of:

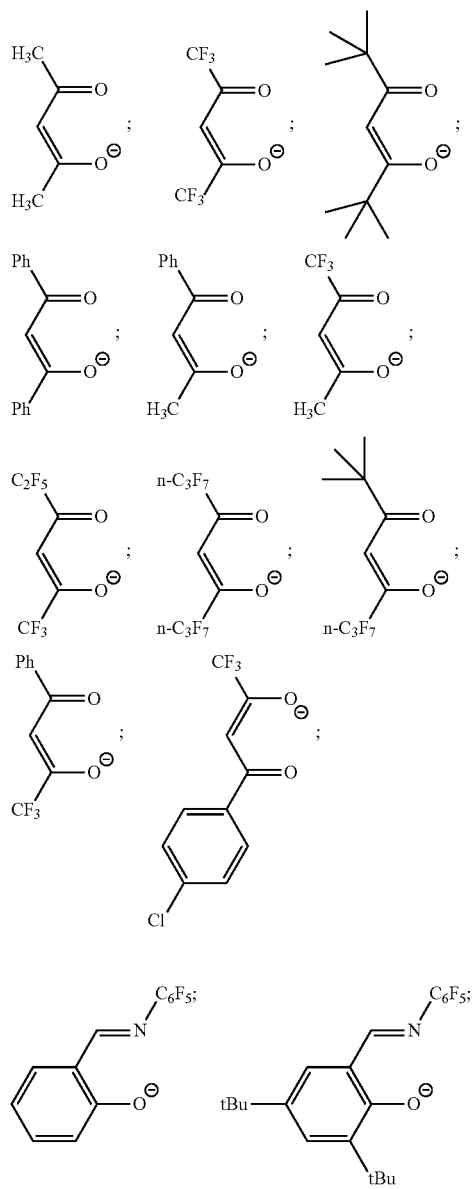

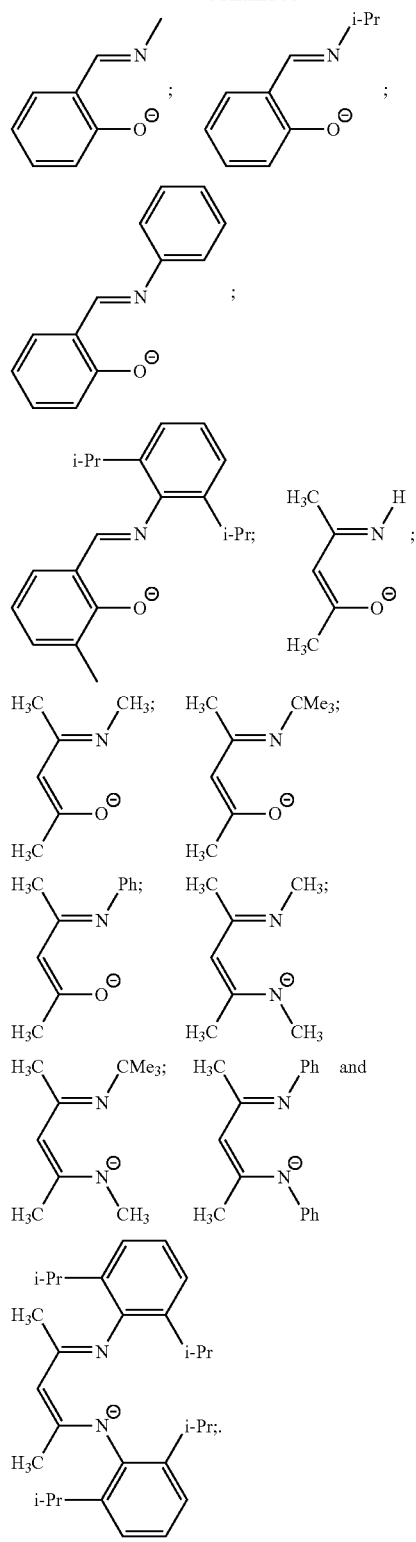

Several of the organopalladium compounds of formula (I) that are suitable to be employed in the compositions of this invention are known in the literature or can be readily made by any of the known procedures in the art. See for example, U.S. Pat. Nos. 7,442,800 B2 and 7,759,439 B2, pertinent portions of which are incorporated herein by reference.

Exemplary organopalladium compounds of formulae (III), (IIIA) or (IIIB) that can be employed in the composition of this invention without any limitation include the following:

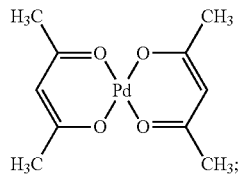

palladium (acetylacetonate)₂
(Pd304)

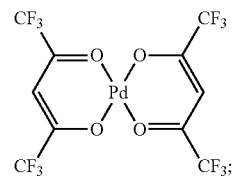

palladium
(hexafluoroacetylacetonate)₂
(Pd520)

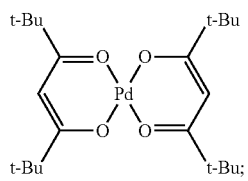

bis(2,2,6,6-tetramethyl-
3,5-heptanedionato)
palladium(II)
(Pd472)

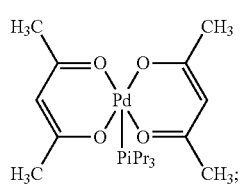

palladium (acetylacetonate)₂
tri-isopropylphosphine

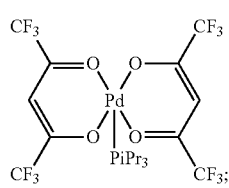

palladium
(hexafluoroacetylacetonate)₂
tri-isopropylphosphine
(Pd(hfac)₂PiPr₃,
Pd680)

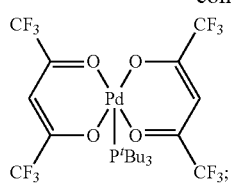

palladium
(hexafluoroacetylacetonate)₂
tri-tert-butylphosphine
(Pd(hfac)₂P(tert-Bu)₃,
Pd722)

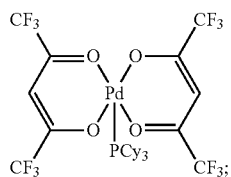

palladium
(hexafluoroacetylacetonate)₂
tri-cyclohexylphosphine
(Pd(hfac)₂PCy₃,
Pd800)

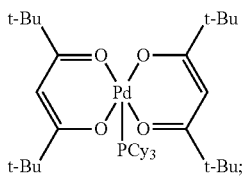

palladium
(tetramethylheptenonoate)₂
tri-cyclohexylphosphine

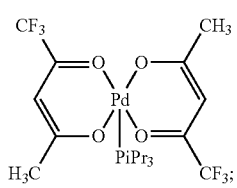

palladium
(trifluoroacetylacetonate)₂
(Pd(tfacac)₂)
tri-isopropylphosphine

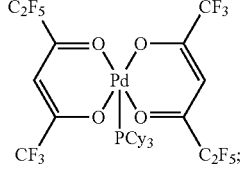

palladium
(pentafluoropropionyl-
trifluoroacetonate)₂
tri-cyclohexylphosphine

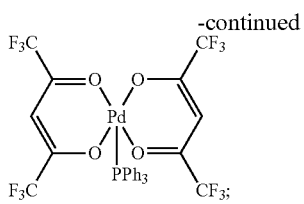

palladium
(hexafluoroacetylacetonate)$_2$
triphenylphosphine
(Pd(hfac)$_2$PPh$_3$, Pd782)

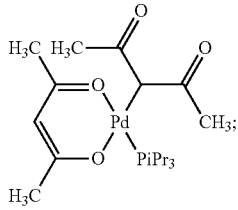

palladium
(acetylacetonate)$_2$
tri-isopropylphosphine
(Pd(acac)$_2$PiPr$_3$,
Pd465)

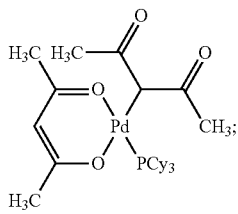

palladium
(acetylacetonate)$_2$
tri-cyclohexylphosphine
(Pd(acac)$_2$PCy$_3$,
Pd585)

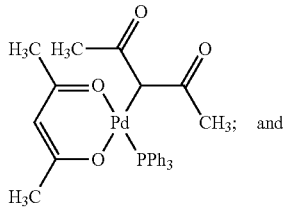

palladium
(acetylacetonate)$_2$
triphenylphosphine
(Pd(acac)$_2$PPh$_3$)

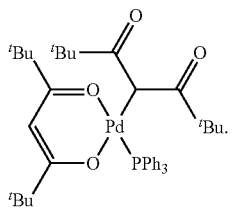

palladium
(2,2,6,6-tetramethylheptane-
3,5-dionate)$_2$
triphenylphosphine

As noted, the composition of this invention further contains a soluble photoacid generator which when combined with the organopalladium compound of formulae (III), (IIIA) or (MB) and a photosensitizer will cause mass polymerization of the monomers contained therein when exposed to suitable radiation as described herein. Any of the known photoacid generators can be used in the compositions of this invention, which would being about this effect, such as for example, certain of the halonium salts, sulfonium salts, and the like.

In some embodiments the soluble photoacid generator of the formula (I$_a$) are employed in the composition of this invention:

Wherein Aryl$_1$ and Aryl$_2$ are the same or different and are independently selected from the group consisting of substituted or unsubstituted phenyl, biphenyl and naphthyl; Hal is iodine or bromine; and An$^\ominus$ is a weakly coordinating anion (WCA) which is weakly coordinated to the cation complex. More specifically, the WCA anion functions as a stabilizing anion to the cation complex. The WCA anion is relatively inert in that it is non-oxidative, non-reducing, and non-nucleophilic. In general, the WCA can be selected from borates, phosphates, arsenates, antimonates, aluminates, boratobenzene anions, carborane, halocarborane anions, sulfonamidate, sulfonates, tris(perfluoro($C_1$-$C_4$)alkanesulfonyl)methide and bis(perfluoro-($C_1$-$C_4$)alkanesulfonyl)imide.

Representative examples of the compounds of formula (I$_a$) may be listed as follows:

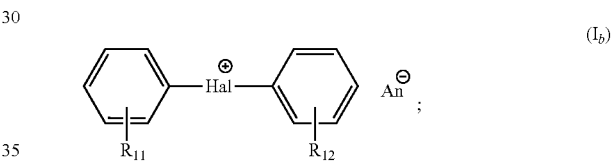

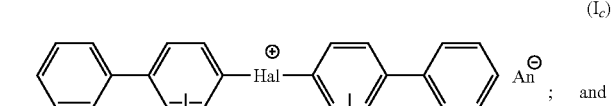

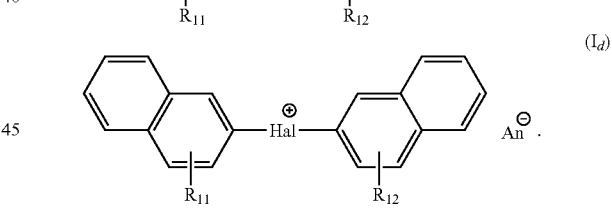

Wherein R$_{11}$ and R$_{12}$ are as defined herein. Similarly various sulfonium salts can be used as photoacid generators, which include broadly compounds of formula (II) as described herein.

Accordingly, non-limiting examples of suitable photoacid generators of formulae (I) or (II) that may be employed in the composition of this invention are listed below:

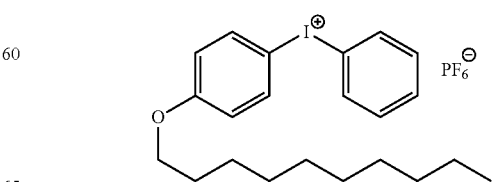

4-(decyloxy)phenyl)(phenyl)iodonium hexafluorophosphate (DPPI-PF$_6$);

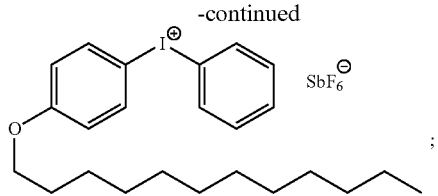

4-(dodecyloxy)phenyl)(phenyl)iodonium hexafluoroantimonate (DoPPI-SBF$_6$)

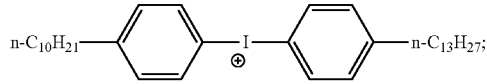

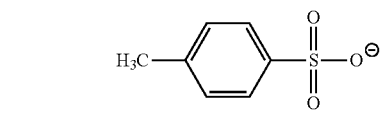

n-decylphenyl-n-tridecylphenyliodonium p-toluenesulfonate

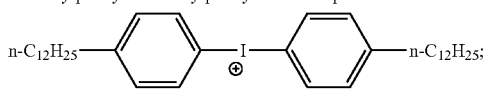

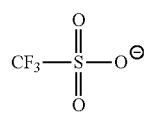

bis(n-dodecylphenyl)iodonium triflate

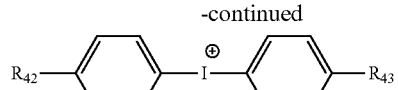

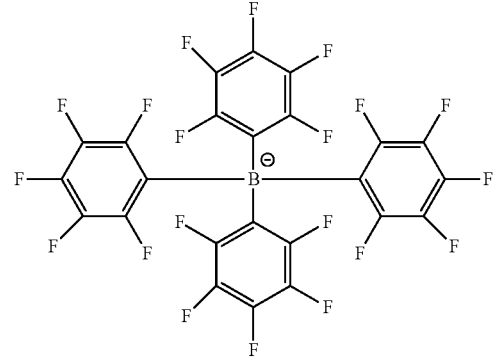

where $R_{42}$ and $R_{43}$ are the same or different and each independently selected from linear or branched ($C_{10}$-$C_{13}$) alkyl, for example iodonium, diphenyl-, 4,4'-di-$C_{10-13}$-alkylphenyl derivatives, tetrakis(2,3,4,5,6-pentafluorophenyl) borates are commercially available under the tradename SILCOLEASE UV CATA 243;

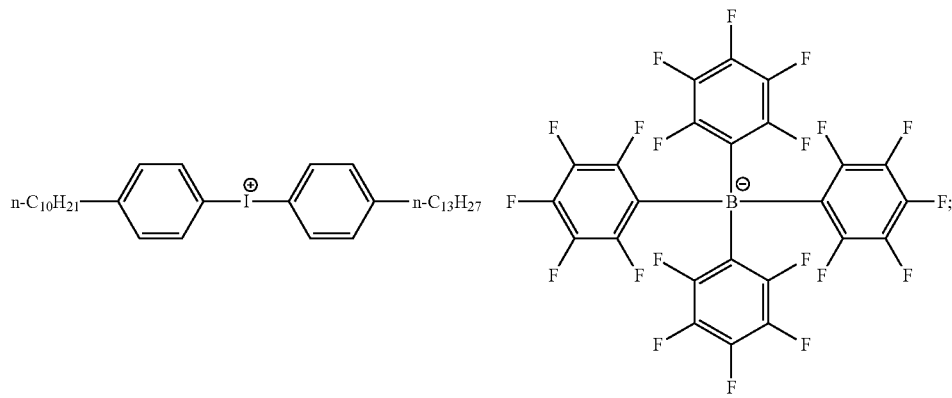

4-n-decylphenyl-4'-n-tridecylphenyliodonium tetrakis(pentafluorophenyl)borate

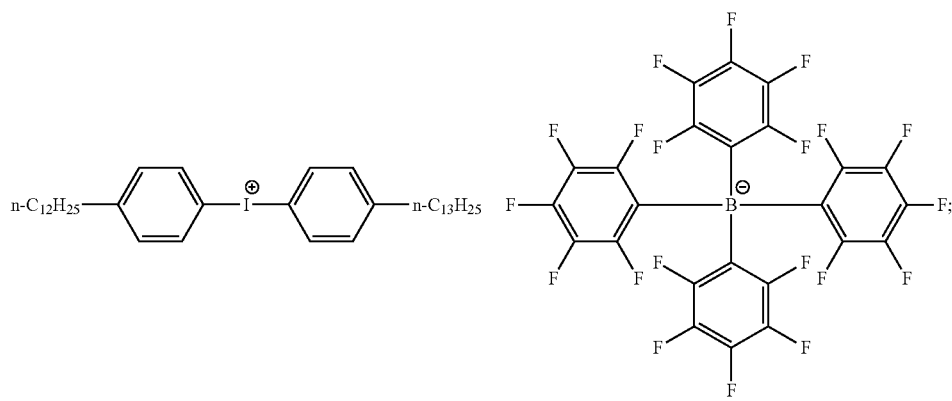

di(4-n-dodecylphenyl)iodonium tetrakis(pentafluorophenyl)borate (PAG2)

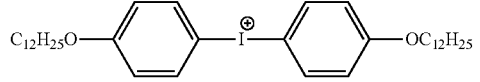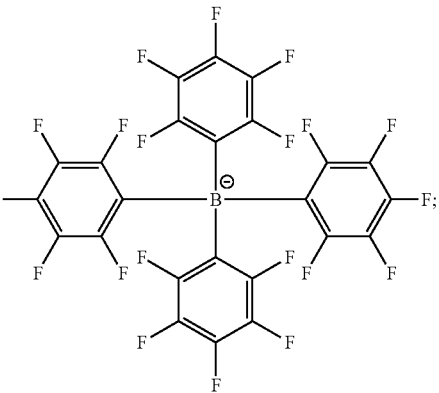

di(4-n-dodecyloxyphenyl)iodonium tetrakis(pentafluorophenyl)borate

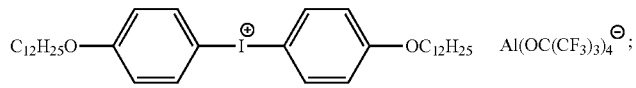

bis(4-dodecylphenyl)iodonium tetrakis
((1,1,1,3,3,3-hexafluoro-2-
(trifluoromethyl)propan-2-yl)oxy)aluminate

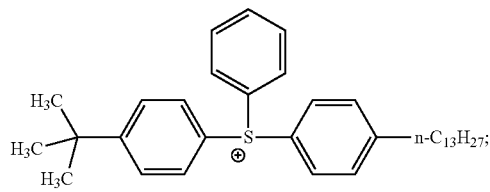

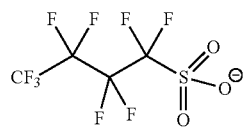

(4-tert-butylphenyl)(phenyl)(4′-tridecylphenyl)
sulfonium perfluoro-1-butanesulfonate

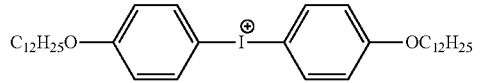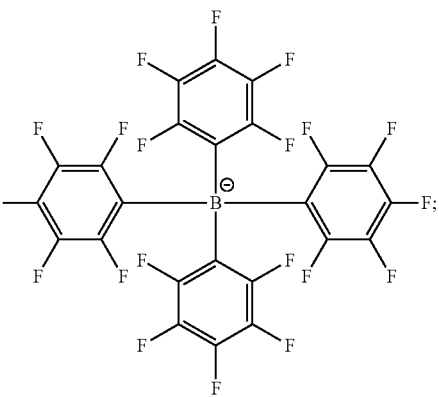

bis(4-(n-dodecyloxy)phenyl)iodonium tetrakis(pertfluorophenyl)borate

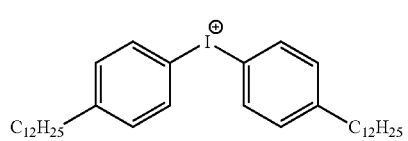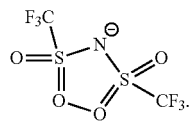

di(dodecylphenyl)iodonium bis(trifluoromethane)sulfonimide

However, any of the other known photoacid generators which can activate the organopalladium compounds of formulae (III), (IIIA) or (MB) as employed herein when exposed to suitable radiation can also be used in the composition of this invention. All such compounds are part of this invention.

As noted, the composition of this invention additionally contains a photosensitizer compound which further facilitates the formation of the active catalyst when the composition is exposed to suitable radiation in the presence of the photoacid generator as employed herein. For this purpose, any suitable sensitizer compound can be employed in the compositions of the present invention, which activates the photoacid generator and/or the organopalladium compound of formulae (III), (IIIA) or Such suitable sensitizer compounds include, anthracenes, phenanthrenes, chrysenes, benzpyrenes, fluoranthenes, rubrenes, pyrenes, xanthones, indanthrenes, thioxanthen-9-ones, and mixtures thereof. In some exemplary embodiments, suitable sensitizer components include a compound of formula (VIII) or a compound of formula (IX):

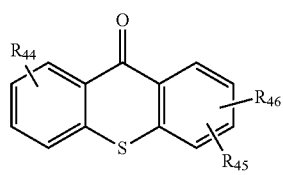

(VIII)

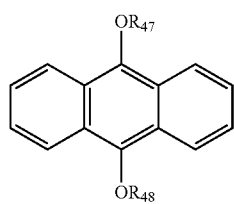

(IX)

wherein $R_{44}$, $R_{45}$ and $R_{46}$ are the same or different and independently of each other selected from the group consisting of hydrogen, halogen, hydroxy, $NO_2$, $NH_2$, methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$alkyl, $(C_6-C_{10})$-aryloxy, $C(O)(C_1-C_6)$alkyl, COOH, $C(O)O(C_1-C_6)$alkyl, and $SO_2(C_6-C_{10})$aryl;

$R_{47}$ and $R_{48}$ are the same or different and independently of each other selected from the group consisting of methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl and $(C_6-C_{10})$aryl$(C_1-C_3)$alkyl.

Representative examples of the compounds of formula (VIII) or the compounds of formula (IX) without any limitation may be listed as follows:

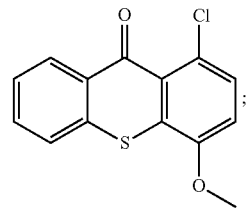

1-chloro-4-methoxy-9H-thioxanthen-9-one

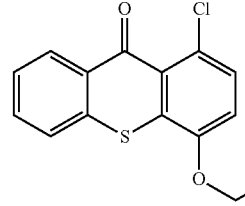

1-chloro-4-ethoxy-9H-thioxanthen-9-one

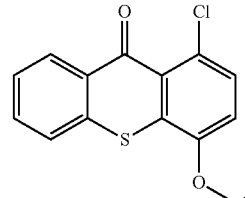

1-chloro-4-propoxy-9H-thioxanthen-9-one
(commercially sold under the name CPTX from Lambson)

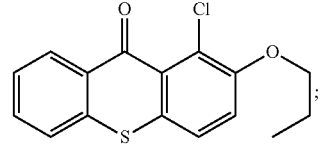

1-chloro-2-propoxy-9H-thioxanthen-9-one

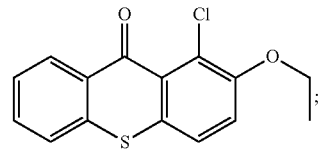

1-chloro-2-ethoxy-9H-thioxanthen-9-one

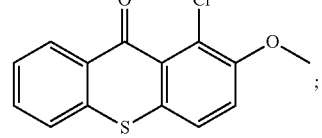

1-chloro-2-methoxy-9H-thioxanthen-9-one

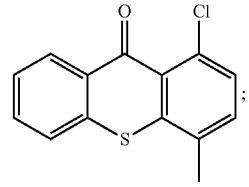

1-chloro-4-methyl-9H-thioxanthen-9-one

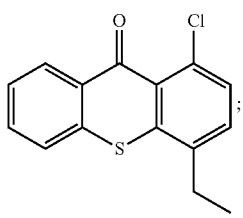

1-chloro-4-ethyl-9H-
thioxanthen-9-one

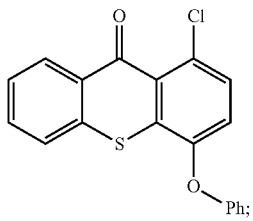

1-chloro-4-phenoxy-9H-
thioxanthen-9-one

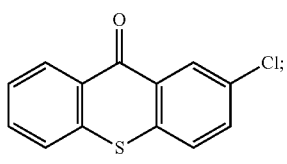

2-chlorothioxanthen-9-one
(CTX)

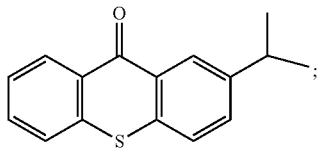

2-isopropyl-9H-thioxanthen-9-one
(ITX)

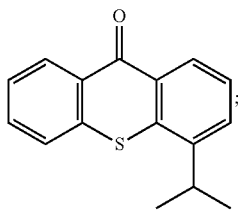

4-isopropyl-9H-
thioxanthen-9-one

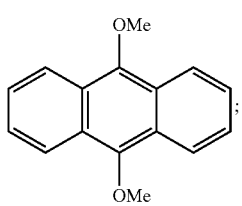

9,10-dimethoxyanthracene
(DMA)

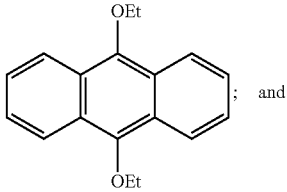

; and 9,10-diethoxyanthracene
(DEA)

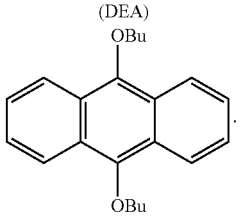

9,10-diethoxyanthracene
(DBA)

Other suitable photosensitizer compounds include various substituted and unsubstituted phenothiazine derivatives, such as for example:

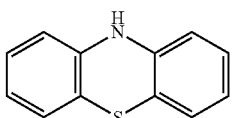

phenothiazine

Generally, photosensitizers absorb energy from the radiated light source and transfers that energy to the desirable substrate/reactant, which in the present invention is the photoacid generator employed in the composition of this invention. In some embodiments the compounds of formula (VIII) or the compounds of formula (IX) can be activated at certain wavelength of the electromagnetic radiation which can generally range from about 240 nm to 410 nm. Accordingly, any of the compounds which are active in this electromagnetic radiation can be employed in the compositions of this invention which are stable to various fabrications methods where the compositions of this invention can be used including for example OLED or the 3D fabrication methods. In some embodiments the wavelength of the radiation to activate the compounds of formulae (VIII) or (IX) is 260 nm. In some other embodiments the wavelength of the radiation to activate the compounds of formula (VIII) or (IX) is 310 nm. In some other embodiments the wavelength of the radiation to activate the compounds of formula (VIII) or (IX) is 365 nm. In yet some other embodiments the wavelength of the radiation to activate the compounds of formula (VIII) or (IX) is 395 nm.

Any amount of organopalladium compound of formulae (III), (IIIA) or (IIIB), the photoacid generator of formulae (I) or (II) and the photosensitizer of formulae (VIII) or (IX) can be employed in the composition of this invention which will bring about the intended result. Generally, the molar ratio of monomer of formula (V):compound of formulae (III), (IIIA) or (IIIB) is in the range of 25,000:1 to 5,000:1 or lower. In some other embodiments such monomer of formula (V): compound of formula (I) is 10,000:1, 15,000:1, 20,000:1 or higher than 30,000:1. It should be noted that monomer of formula (V) as mentioned herein may include one or more monomers of formula (V) distinct from each other and may additionally contain one or more monomers of formulae (VI) or (VII), and therefore, the above ratio represents combined molar amounts of all such monomers employed. Similarly, the molar ratio of organopalladium compound of formulae (III), (IIIA) or (IIIB):the photoacid generator of formulae (I) or (II):the photosensitizer of formulae (VIII) or (IX) is in the range of 1:1:0.5 to 1:2:2 or 1:2:1 or 1:4:1, 1:2:4, 1:1:2, 1:4:2 or such ranges which will bring about the intended benefit.

Advantageously, it has further been found that the composition according to this invention forms a substantially transparent film when exposed to a suitable actinic radiation (UV irradiation). That is to say that when the composition of this invention is exposed to certain actinic radiation, the monomers undergo mass polymerization to form films which are substantially transparent to visible light. That is, most of the visible light is transmitted through the film. In some embodiments such film formed from the composition of this invention exhibits a transmission of equal to or higher than 90 percent of the visible light. In some other embodiments such film formed from the composition of this invention exhibits a transmission of equal to or higher than 95 percent of the visible light. It should be further noted that any actinic radiation that is suitable to carry out this mass polymerization can be employed, such as for example, exposure to any actinic radiation in the wavelength of 200 nm to 400 nm. However, any radiation higher than 400 nm can also be employed. In some embodiments the wave length of the actinic radiation employed is 250 nm, 295 nm, 360 nm, 395 nm or higher than 400 nm.

In some other embodiments the composition of this invention undergoes mass polymerization when exposed to suitable actinic radiation and heat to form a substantially transparent film. In yet other embodiments the composition of this invention undergoes mass polymerization when exposed to suitable UV irradiation at a temperature from 50° C. to 100° C. to form a substantially transparent film.

Accordingly, exemplary compositions of this invention without any limitation may be enumerated as follows:

5-hexylbicyclo[2.2.1]hept-2-ene (HexylNB), palladium hexafluoroacetylacetonate (Pd520), 4,4'-di-$C_{10\text{-}13}$-alkylphenyl derivatives, tetrakis(2,3,4,5,6-pentafluorophenyl)borates (PAG1) and 2-isopropyl-9H-thioxanthen-9-one (ITX);

5-hexylbicyclo[2.2.1]hept-2-ene (HexylNB), 5-(2-([1,1'-biphenyl]-2-yloxy)ethyl)bicyclo[2.2.1]hept-2-ene (NBE-tOPhPh), palladium hexafluoroacetylacetonate (Pd520), 4,4'-di-$C_{10\text{-}13}$-alkylphenyl derivatives, tetrakis(2,3,4,5,6-pentafluorophenyl)borates (PAG1) and 2-isopropyl-9H-thioxanthen-9-one (ITX);

5-decylbicyclo[2.2.1]hept-2-ene (DecNB), 5-(2-([1,1'-biphenyl]-2-yloxy)ethyl)bicyclo[2.2.1]hept-2-ene (NBE-tOPhPh), bis(2,2,6,6-tetramethyl-3,5-heptanedionato)palladium(II) (Pd472), bis(4-n-dodecylphenyl)iodonium tetrakis(pentafluorophenyl)borate (PAG2) and 2-chloro-9H-thioxanthen-9-one (CTX);

5-decylbicyclo[2.2.1]hept-2-ene (DecNB), bis(2,2,6,6-tetramethyl-3,5-heptanedionato)palladium(II) (Pd472), di(4-n-dodecylphenyl)iodonium tetrakis(pentafluorophenyl)borate (PAG2) and 2-chloro-9H-thioxanthen-9-one (CTX); and 5-hexylbicyclo[2.2.1]hept-2-ene (HexylNB), palladium hexafluoroacetylacetonate (Pd520), di(4-n-dodecylphenyl) iodonium tetrakis(pentafluorophenyl)borate (PAG2) and 2-isopropyl-9H-thioxanthen-9-one (ITX).

In a further aspect of this invention there is provided a kit for forming a substantially transparent film. There is dispensed in this kit a composition of this invention. Accordingly, in some embodiments there is provided a kit in which there is dispensed one or more olefinic monomers of formula (V) as described herein; an organopalladium compound of formula (III) or an organopalladium compound of formula (IIIA) or an organopalladium compound of formula (IIIB) as described herein; a photoacid generator of formulae (I) or (II) as described herein and a photosensitizer of formulae (VIII) or (IX). In some embodiments the kit of this invention contains one or more monomers of formula (V) optionally in combination with one or more monomers of formulae (VI) or (VII) so as to obtain a desirable result and/or for an intended purpose.

In some embodiments, the aforementioned kit encompasses one or more monomers of formula (V) and one or more monomers of formulae (VI) or (VII). In some other embodiments the kit of this invention encompasses at least two monomers wherein first monomer serves as a solvent for the second monomer. Any of the monomers of formulae (V) to (VII) as described herein can be used in this embodiment. The molar ratio of such two monomers contained in these embodiments can vary and may range from 1:99 to 99:1, or 10:90 to 90:10, 20:80 to 80:20, 30:70 to 70:30, 60:40 to 40:60 or 50:50, and so on. In some other embodiments the kit may encompass a composition wherein dispensed two monomers which could be one monomer of formula (V) and another monomer of formula (VI). Further, the monomer of formula (VI) is completely soluble in monomer of formula (V) to form a clear solution at room temperature. In some embodiments the monomer mixture may become a clear solution at slightly elevated temperature, such as for example, 30° C. or 40° C. or 50° C., before they undergo mass polymerization.

In another aspect of this embodiment of this invention the kit of this invention undergoes mass polymerization when exposed to suitable actinic radiation for a sufficient length of time to form a polymeric film. That is to say that the composition of this invention is poured onto a surface or onto a substrate which needs to be encapsulated and exposed to suitable radiation in order for the monomers to undergo polymerization to form a solid transparent polymer which could be in the form of a transparent film. Generally, as already noted above, such polymerization can take place at various wavelengths of actinic radiation, such as for example, at 265 nm 315 nm 365 nm or 395 nm and so on. The mass polymerization may further be accelerated by heating, which can also be in stages, for example heating to 40° C. or 50° C. or 60° C. for 5 minutes each, and if necessary further heating to 70° C. for various lengths of time such as from 5 minutes to 15 minutes and so on. By practice of this invention it is now possible to obtain polymeric films on such substrates which are substantially transparent film. The "substantially transparent film" as used herein means that the films formed from the composition of this invention are optically clear in the visible light. Accordingly, in some embodiments of this invention such films are having at least 90 percent of visible light transmission, in some other embodiments the films formed from the composition of this invention exhibit at least 95 percent of visible light transmission.

In some embodiments of this invention the kit as described herein encompasses a composition which further contains one or more monomers selected from a monomer of formula (VI) or a monomer of formula (VII) as described hereinabove. Again, any of the monomers of formula (VI) or (VII) as described herein can be used in this embodiment, and in any desirable amounts depending on the nature of the intended use.

In some embodiments, the kit as described herein encompasses various exemplary compositions as described hereinabove.

In yet another aspect of this invention there is further provided a method for forming a substantially transparent film for the fabrication of a variety of optoelectronic device comprising:

forming a homogeneous clear composition comprising one or more monomers of formula (V); an organopalladium compound of formula (III) or an organopalladium compound of formula (IIIA) or an organopalladium compound of formula (MB); a photoacid generator of formulae (I) or (II); and a photosensitizer of formulae (VIII) or (IX);

coating a suitable substrate with the composition or pouring the composition onto a suitable substrate to form a film; and exposing the film to a suitable actinic radiation to cause polymerization of the monomers.

The coating of the desired substrate to form a film with the composition of this invention can be performed by any of the coating procedures as described herein and/or known to one skilled in the art, such as by spin coating. Other suitable coating methods include without any limitation spraying, doctor blading, meniscus coating, ink jet coating and slot coating. The mixture can also be poured onto a substrate to form a film. Suitable substrate includes any appropriate substrate as is, or may be used for electrical, electronic or optoelectronic devices, for example, a semiconductor substrate, a ceramic substrate, a glass substrate.

Next, the coated substrate is exposed to suitable radiation as described herein. Alternatively, the coated substrate is baked, i.e., heated to facilitate the mass polymerization, for example to a temperature from 50° C. to 100° C. for about 1 to 60 minutes, although other appropriate temperatures and times can be used. In some embodiments the substrate is baked at a temperature of from about 60° C. to about 90° C. for 2 minutes to 10 minutes. In some other embodiments the substrate is baked at a temperature of from about 60° C. to about 90° C. for 5 minutes to 20 minutes.

The films thus formed are then evaluated for their optical properties using any of the methods known in the art. For example, the refractive index of the film across the visible spectrum can be measured by ellipsometry. The optical quality of the film can be determined by visual observation. Quantitatively the percent transparency can be measured by visible spectroscopy. Generally, the films formed according to this invention exhibit excellent optical transparent properties and can be tailored to desirable refractive index as described herein.

Accordingly, in some of the embodiments of this invention there is also provided an optically transparent film obtained by the mass polymerization of the composition as described herein. In another embodiment there is also provided an optoelectronic device comprising the transparent film of this invention as described herein.

In yet some other embodiments the composition of this invention can also be used in a variety of photo induced nanoimprint lithography (NIL), such as for example, UV-NIL. For instance, the compositions of this invention can be used in a variety of photocurable imprint technology. Typically in such applications, the composition of this invention is suitably placed on a substrate (for example by coating or similar means), which is then covered by a suitable stamp and exposed to radiation so as to allow the composition of this invention to cure to a solid. The stamp is then released to obtain the nano-imprinted film. Such substrates can include for example a master digital video disk (DVD).

The following examples are detailed descriptions of methods of preparation and use of certain compounds/monomers, polymers and compositions of the present invention. The detailed preparations fall within the scope of, and serve to exemplify, the more generally described methods of preparation set forth above. The examples are presented for illustrative purposes only, and are not intended as a restriction on the scope of the invention. As used in the examples and throughout the specification the ratio of monomer to catalyst is based on a mole to mole basis.

EXAMPLES

The following abbreviations have been used hereinbefore and hereafter in describing some of the compounds, instruments and/or methods employed to illustrate certain of the embodiments of this invention:
NBEtOPhPh—5-(2-([1,1'-biphenyl]-2-yloxy)ethyl)bicyclo[2.2.1]hept-2-ene; HexylNB—5-hexylbicyclo[2.2.1]hept-2-ene; Pd520—palladium hexafluoroacetylacetonate; Pd472—-bis(2,2,6,6-tetramethyl-3,5-heptanedionato)palladium(II); Rhodorsil PI 2074—tolylcumyliodonium-tetrakis pentafluorophenylborate; PAG1—4,4'-di-$C_{10\text{-}13}$-alkylphenyl derivatives, tetrakis(2,3,4,5,6-pentafluorophenyl)borates; PAG2—bis(4-n-dodecylphenyl)iodonium tetrakis(pentafluorophenyl)borate; PAG3—di(dodecylphenyl)iodonium bis(trifluoromethane)sulfonimide; Rhodorsil 2074®—tolylcumyliodonium-tetrakis pentafluorophenylborate; ITX—4-isopropylthioxanthone; CTX—4-chlorothioxanthone; DCM—dichloromethane; cP—centipoise; DSC—differential scanning calorimetry.

Various monomers as used herein are either commercially available or can be readily prepared following the procedures as described in U.S. Pat. No. 9,944,818.

Various organopalladium compounds of formula (I) as used herein are known in the literature and can be readily prepared following the procedures as described in the literature. Various photoacid generators as used herein are either available commercially or can be readily prepared following the procedures as described hereinbelow in Examples A to C.

Example A

Bis(4-n-dodecylphenyl)iodonium tetrakis(pentafluorophenyl)borate (PAG2)

In a suitable reaction vessel equipped with a magnetic stirrer was placed a mixture of 1-phenyldodecane (34.5 g, 140 mmol), potassium periodate (15 g, 70 mmol), acetic anhydride (30 g, 294 mmol) and acetic acid (10 g). The reaction mixture was cooled with an ice bath. To this solution carefully was added dropwise a solution of sulfuric acid (16 g) dissolved in acetic anhydride (20 g). After the addition, reaction mixture was stirred overnight. Then, water (20 ml) was added followed by an aqueous solution of NaCl (10.2 g, 170 mmol dissolved in 50 ml of water). The reaction mixture was cooled to 0° C. and the resulting precipitate was collected.

The precipitate was then washed with cold isopropanol and methanol and air dried overnight to obtain di(p-dodecylphenyl)iodonium chloride (13 g, 31% yield). The precipitate thus obtained was then dispersed in dichloromethane (5 ml) and to this was added lithium tetrakis(pentafluorophenyl)borate dissolved in dichloromethane (20 ml). The mixture was stirred for 30 minutes and an additional 50 ml of dichloromethane was added. The reaction mixture was filtered using a 0.45 µm PTFE filter. Removed solvent in vacuo to obtain bis(4-n-dodecylphenyl)iodonium tetrakis (pentafluorophenyl)borate (PAG2, 18.4 g 70% yield).

Example B

Bis(4-dodecylphenyl)iodonium tetrakis((1,1,1,3,3,3-hexafluoro-2-(trifluoromethyl)propan-2-yl)oxy)aluminate In a suitable reaction vessel was placed di(dodecylphenyl) iodonium chloride (0.67 g, 1.03 mmol) dispersed in dichloromethane (~5 ml). This dispersion was added in 1 ml increments to a solution of lithium tetrakis(perfluoro-tert-butoxy) aluminate (1 g, 1.03 mmol) dissolved in a mixture of acetone (2 ml) and dichloromethane (25 ml). The resulting mixture was stirred for 25 minutes then filtered through a 5 µm nylon syringe filter. After filtering, the solvent was removed in vacuo and the residue was re-dissolved in dichloromethane (5 ml). This solution was filtered through a 5 µm nylon syringe filter. After filtering, the solvent was removed in vacuo to obtain the tile compound: 1.53 g (94% yield)

Example C

Di(dodecylphenyl)iodonium Bis(trifluoromethane)sulfonimide

In a suitable reaction vessel was dispersed didodecylphenyliodonium chloride (1 g, 1.53 mmol) in 5 ml of DCM. To this dispersion was added a solution of lithium bis(trifluoromethane)sulfonimide (0.44 g, 1.53 mmol) dissolved in 5 ml of a 1:1 mixture of DCM and ethyl acetate. After the lithium bis(trifluoromethane)sulfonimide addition, the reaction mixture was stirred for an additional 30 minutes and then an additional 15 ml of DCM was added to the mixture. The reaction mixture was filtered using a 0.45 µm PTFE syringe filter and the solvent was removed in vacuo. The resulting residue was redissolved in DCM and filtered again through 0.45 µm PTFE syringe filter. The DCM was removed in vacuo to give 1.19 g (86%) of di(dodecylphenyl) iodonium bis(trifluoromethane)sulfonimide (PAG3).

The following Examples 1 to 5 demonstrate the benefits obtained by the soluble photoacid generators in accordance with this invention.

Example 1

Mass Polymerization of HexylNB with Pd800

In a glass bottle, Pd520(1 molar part), PAG1 (3 molar parts), ITX (1 molar part) were dissolved in HexylNB (4000 molar parts) under sonication to form a clear solution. This solution was then UV light exposed for 4 sec (2 J/cm$^2$, 395 nm) at room temperature. The solution turned into a film indicating the monomer was polymerized, as also confirmed by UV-DSC.

Example 2

The procedures of Example 1 were substantially followed in this Example 2 except for using 4500 molar parts of HexylNB and 4 molar parts of PAG1. The solution turned into film upon exposure to UV light for 4 sec (2 J/cm$^2$, 395 nm) at room temperature.

Example 3

The procedures of Example 1 were substantially followed in this Example 3 except for using 4500 molar parts of HexylNB, 500 molar parts of NBEtOPhPh and 4 molar parts of PAG1. The solution turned into film upon exposure to UV light for 4 sec (2 J/cm$^2$, 395 nm) at room temperature.

Example 4

The procedures of Example 1 were substantially followed in this Example 4 except for using 5000 molar parts of HexylNB and 5 molar parts of PAG1. The heat of reaction as measured by UV-DSC was about 356 J/g.

Example 5

The procedures of Example 1 were substantially followed in this Example 5 except for using 5000 molar parts of HexylNB and 5 molar parts of PAG2. The heat of reaction as measured by UV-DSC was about 316 J/g.

The following Comparative Examples 1-2 demonstrate that use of other readily available iodonium salts, such as for example, Rhodorsil 2074® as the photoacid generator results in no polymerization of the monomers.

Comparative Example 1

The procedures of Example 1 were substantially followed in this Comparative Example 1 except for using 4 molar parts of Rhodorsil 2074. Rhodorsil 2074 was not completely miscible in HexylNB. No reaction was observed upon exposure to UV light for 4 sec (2 J/cm$^2$, 395 nm) at room temperature as evidenced by the reaction mixture remained in the liquid form. The UV-DSC of a portion of the sample further confirmed formation of no exotherm at elevated temperatures.

Comparative Example 2

The procedures of Example 3 were substantially followed in this Comparative

Example 2 except for using 4 molar parts of Rhodorsil 2074. Rhodorsil 2074 was not completely miscible in the monomeric mixture. No reaction was observed upon exposure to UV light for 4 sec (2 J/cm$^2$, 395 nm) at room temperature as evidenced by the reaction mixture remained in the liquid form. The UV-DSC of a portion of the sample further confirmed formation of no exotherm at elevated temperatures.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A composition comprising:
   a) a soluble photoacid generator selected from the group consisting of a compound of formula (I):

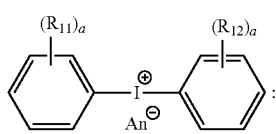

and a compound of formula (II):

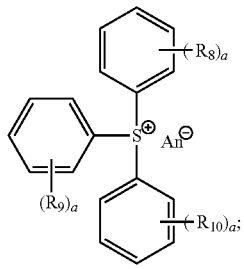

wherein:
$a$ is an integer from 1 to 5;
$An^{\ominus}$ is selected from the group consisting of $Cl^{\ominus}$, $Br^{\ominus}$, $I^{\ominus}$, $BF_4^{\ominus}$, tetrakis(pentafluorophenyl)borate, tetrakis(3,5-bis(trifluoromethyl)phenyl)borate, tetrakis(2-fluorophenyl)borate, tetrakis(3-fluorophenyl)borate, tetrakis(4-fluorophenyl)borate, tetrakis(3,5-difluorophenyl)borate, tetrakis(2,3,4,5-tetrafluorophenyl)borate, tetrakis(3,4,5,6-tetrafluorophenyl)borate, tetrakis(3,4,5-trifluorophenyl)borate, methyltris(perfluorophenyl)borate, ethyltris(perfluorophenyl)borate, phenyltris(perfluorophenyl)borate, tetrakis(1,2,2-trifluoroethylenyl)borate, tetrakis(4-tri-1-propylsilyltetrafluorophenyl)borate, tetrakis(4-dimethyl-tert-butylsilyltetrafluorophenyl)borate, (triphenylsiloxy)tris(pentafluorophenyl)borate, (octyloxy)tris(pentafluorophenyl)borate, tetrakis[3,5-bis[1-methoxy-2,2,2-trifluoro-1-(trifluoromethyl)ethyl]pheny-l]borate, tetrakis[3-[1-methoxy-2,2,2-trifluoro-1-(trifluoromethyl)ethyl]-5-(trifluoromethyl)phenyl]borate, and tetrakis[3-[2,2,2-trifluoro-1-(2,2,2-trifluoroethoxy)-1-(trifluoromethyl)-ethyl]-5-(trifluoromethyl)phenyl]borate, $PF_6^{\ominus}$, $SbF_6^{\ominus}$, $n\text{-}C_4F_9SO_3^{\ominus}$, $CF_3SO_3^{\ominus}$ and $p\text{-}CH_3(C_6H_4)\text{—}SO_3^{\ominus}$;
at least one of $R_8$, $R_9$, $R_{10}$, $R_{11}$ and $R_{12}$ is selected from the group consisting of linear or branched $(C_{10}\text{-}C_{20})$ alkyl, $(C_6\text{-}C_{10})$aryl$(C_{10}\text{-}C_{20})$alkyl, $(C_{10}\text{-}C_{20})$alkoxy, $(C_6\text{-}C_{10})$aryloxy$(C_{10}\text{-}C_{20})$alkyl, $(C_{10}\text{-}C_{20})$alkanoyl$(C_6\text{-}C_{10})$aryl and $(C_{10}\text{-}C_{20})$alkoxy$(C_6\text{-}C_{10})$aroyl$(C_6\text{-}C_{20})$alkyl; and
the remaining $R_8$, $R_9$, $R_{10}$, $R_{11}$ and $R_{12}$ are the same or different and each independently selected from the group consisting of halogen, methyl, ethyl, linear or branched $(C_3\text{-}C_{20})$alkyl, $(C_3\text{-}C_{12})$cycloalkyl, $(C_6\text{-}C_{12})$bicycloalkyl, $(C_7\text{-}C_{14})$tricycloalkyl, $(C_6\text{-}C_{10})$aryl, $(C_6\text{-}C_{10})$aryl$(C_1\text{-}C_3)$alkyl, $(C_1\text{-}C_{12})$alkoxy, $(C_3\text{-}C_{12})$cycloalkoxy, $(C_6\text{-}C_{12})$bicycloalkoxy, $(C_7\text{-}C_{14})$tricycloalkoxy, $(C_6\text{-}C_{10})$aryloxy$(C_1\text{-}C_3)$alkyl, $(C_6\text{-}C_{10})$-aryloxy, $(C_6\text{-}C_{10})$thioaryl, $(C_1\text{-}C_6)$alkanoyl$(C_6\text{-}C_{10})$thioaryl, $(C_1\text{-}C_6)$alkoxy$(C_6\text{-}C_{10})$aroyl$(C_1\text{-}C_6)$alkyl and $(C_6\text{-}C_{10})$thioaryl-$(C_6\text{-}C_{10})$diarylsulfonium salt;

b) an organopalladium compound selected from the group consisting of a compound of formula (III), a compound of formula (IIIA) and a compound of formula (IIIB):

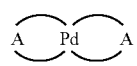

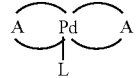

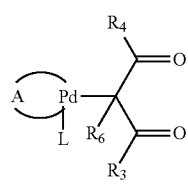

wherein:
L is a ligand selected from the group consisting of $P(R)_3$, $P(OR)_3$, $O\text{=}P(R)_3$, RCN and substituted or unsubstituted pyridines, where R is selected from the group consisting of methyl, ethyl, linear or branched $(C_3\text{-}C_{16})$alkyl, $(C_1\text{-}C_{16})$perfluoroalkyl, $(C_3\text{-}C_{10})$cycloalkyl, $(C_6\text{-}C_{10})$aryl$(C_1\text{-}C_{16})$alkyl and substituted or unsubstituted $(C_6\text{-}C_{10})$aryl;
each A independently is a bidentate monoanionic ligand of formula (IV):

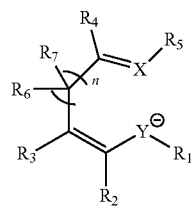

wherein:
$n$ is an integer 0, 1 or 2;
X and Y are independently of each other selected from O, N and S;
$R_1$, $R_2$, $R_3$, $R_4$, $R_5$, $R_6$ and $R_7$ are the same or different and each independently selected from the group consisting of hydrogen, methyl, ethyl, linear or branched $(C_3\text{-}C_{16})$alkyl, $(C_1\text{-}C_{16})$perfluoroalkyl, $(C_3\text{-}C_{10})$cycloalkyl, $(C_6\text{-}C_{10})$aryl$(C_1\text{-}C_{16})$alkyl and substituted or unsubstituted $(C_6\text{-}C_{10})$aryl; provided when either X or Y is O or S, $R_1$ and $R_5$, respectively, do not exist;

c) one or more olefinic monomers of the formula (V):

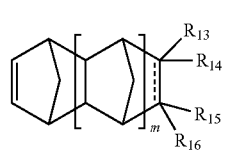

wherein:

m is an integer 0, 1 or 2;

----- is a single bond or a double bond;

at least one of $R_{13}$, $R_{14}$, $R_{15}$ and $R_{16}$ is selected from the group consisting of linear or branched $(C_6-C_{16})$alkyl, $(C_6-C_{12})$aryl$(C_1-C_{16})$alkyl, $(C_6-C_{10})$aryloxy$(C_2-C_{16})$alkyl and $(C_6-C_{10})$aryl$(C_6-C_{10})$aryloxy$(C_1-C_{16})$alkyl;

the remaining $R_{13}$, $R_{14}$, $R_{15}$ and $R_{16}$ are the same or different and each independently selected from the group consisting of hydrogen, halogen, a hydrocarbyl or halohydrocarbyl group selected from methyl, ethyl, linear or branched $(C_3-C_{16})$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_6)$alkyl, methoxy, ethoxy, linear or branched $(C_3-C_{16})$alkoxy, perfluoro$(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy, $(C_6-C_{10})$aryl$(C_1-C_6)$alkoxy, perfluoro$(C_6-C_{10})$aryloxy, perfluoro$(C_6-C_{10})$aryl$(C_1-C_3)$alkoxy, a group of formula (A):

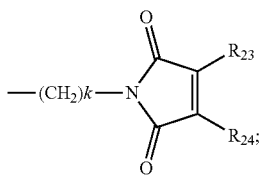

(A)

a group of formula (A1):

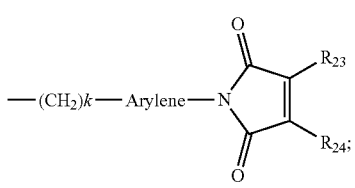

(A1)

a group of formula (A2):

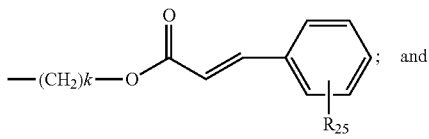

(A2)

a group of formula (A3):

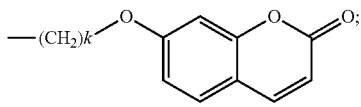

(A3)

and a group of formula (A4):

(A4)

—(CH₂)k—O wherein:

Z is selected from the group consisting of:
O, CO, C(O)O, OC(O), OC(O)O, S, $(CR_{17}R_{18})_b$, $O(CR_{17}R_{18})_b$, $(CR_{17}R_{18})_bO$, $C(O)(CR_{17}R_{18})_b$, $(CR_{17}R_{18})_bC(O)$, $C(O)O(CR_{17}R_{18})_b$, $(CR_{17}R_{18})_bC(O)O$, $OC(O)(CR_{17}R_{18})_b$, $(CR_{17}R_{18})_bOC(O)$, $(CR_{17}R_{18})_bOC(O)O$, $(CR_{17}R_{18})_bOC(O)O(CR_{17}R_{18})_b$, $OC(O)O(CR_{17}R_{18})_b$, $S(CR_{17}R_{18})_b$, $(CR_{17}R_{18})_bS$, $(SiR_{17}R_{18})_b$, $O(SiR_{17}R_{18})_b$, $(SiR_{17}R_{18})_bO$, where $R_{17}$ and $R_{18}$ are the same or different and each independently selected from hydrogen, methyl, ethyl, linear or branched $(C_3-C_{12})$alkyl, substituted or unsubstituted $(C_6-C_{14})$aryl, methoxy, ethoxy, linear or branched $(C_3-C_6)$alkyloxy, $(C_2-C_6)$acyl, $(C_2-C_6)$acyloxy, and substituted or unsubstituted $(C_6-C_{14})$aryloxy; and b is an integer from 0 to 12, inclusive;

Aryl is selected from the group consisting of substituted or unsubstituted phenyl, substituted or unsubstituted biphenyl and substituted or unsubstituted naphthyl, substituted or unsubstituted terphenyl, substituted or unsubstituted anthracenyl substituted or unsubstituted fluorenyl, wherein said substituents are selected from the group consisting of halogen, methyl, ethyl, linear or branched $(C_3-C_6)$alkyl, perfluoro$(C_1-C_{12})$alkyl, $(C_3-C_{12})$cycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_6)$alkyl, methoxy, ethoxy, linear or branched $(C_3-C_{16})$alkoxy, perfluoro$(C_1-C_{12})$alkoxy, $(C_3-C_{12})$cycloalkoxy, $(C_6-C_{10})$aryloxy, $(C_6-C_{10})$aryl$(C_1-C_6)$alkoxy, perfluoro $(C_6-C_{10})$aryloxy and perfluoro$(C_6-C_{10})$aryl$(C_1-C_3)$alkoxy;

k is an integer from 1 to 12;

$R_{23}$, $R_{24}$ and $R_{25}$ are the same or different and each independently selected from the group consisting of hydrogen, methyl, ethyl, linear or branched $(C_3-C_{12})$alkyl, perfluoro$(C_1-C_{12})$alkyl, methoxy, ethoxy, linear or branched $(C_3-C_{12})$alkoxy, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl and perfluoro$(C_6-C_{10})$aryl$(C_1-C_6)$alkyl; or $R_{23}$ and $R_{24}$ taken together with the intervening carbon atoms to which they are attached to form a substituted or unsubstituted $(C_5-C_{14})$cyclic, $(C_5-C_{14})$bicyclic or $(C_5-C_{14})$tricyclic ring; and Arylene is substituted or unsubstituted bivalent $(C_6-C_{14})$aryl;

or one of $R_{13}$ and $R_{14}$ taken together with one of $R_{15}$ and $R_{16}$ and the carbon atoms to which they are attached to form a substituted or unsubstituted $(C_5-C_{14})$cyclic, $(C_5-C_{14})$bicyclic or $(C_5-C_{14})$tricyclic ring;

and m) a photosensitizer.

2. The composition according to claim 1, wherein said olefinic monomer of formula (V) is having:

m=0 or 1;

----- is a single bond;

at least one of $R_{13}$, $R_{14}$, $R_{15}$ and $R_{16}$ is selected from the group consisting of n-hexyl, n-heptyl, n-octyl, n-nonyl, n-decyl, n-dodecyl, phenylbutyl, phenoxyethyl, biphenyloxyethyl and biphenyloxybutyl.

3. The composition according to claim 1, wherein said composition comprises at least two different monomers of formula (V) and is in a clear liquid state having a viscosity below 100 centipoise.

4. The composition according to claim 1, wherein said composition contains said two distinctive monomers of formula (V) in a molar ratio of from 1:99 to 99:1.

5. The composition according to claim 1, wherein said composition forms a substantially transparent film when exposed to suitable actinic radiation.

6. The composition according to claim 5, wherein said film has a transmission of equal to or higher than 90 percent of the visible light.

7. The composition according to claim 1, wherein said bidentate monoanionic ligand is selected from the group consisting of:

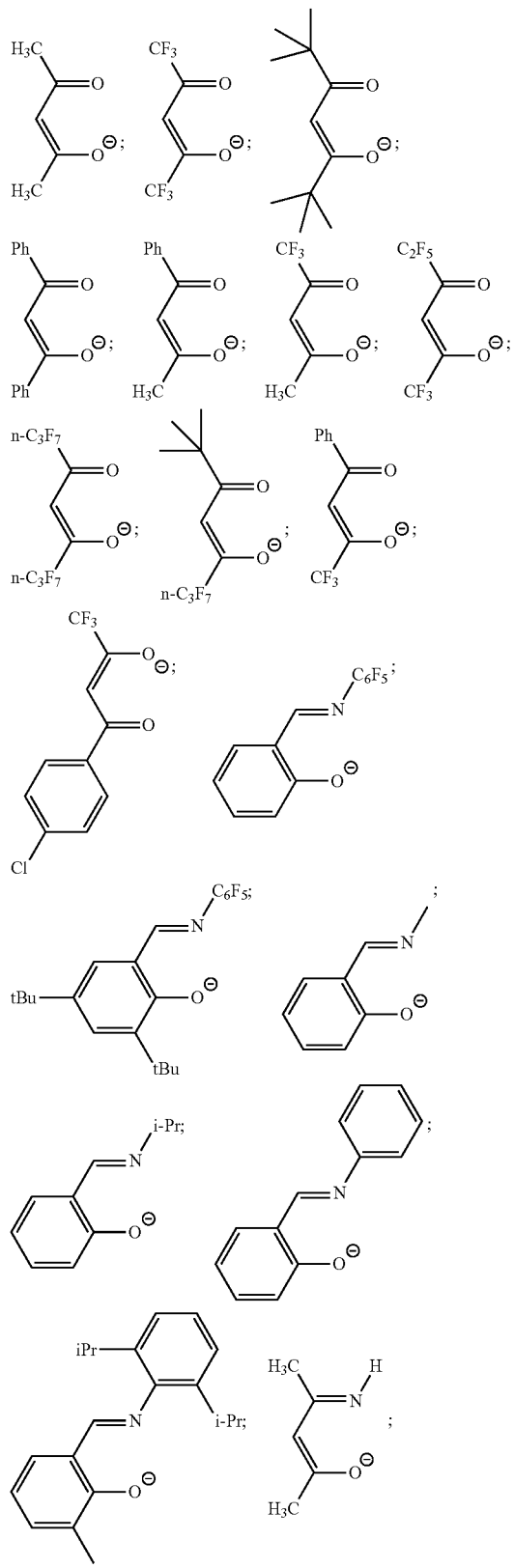

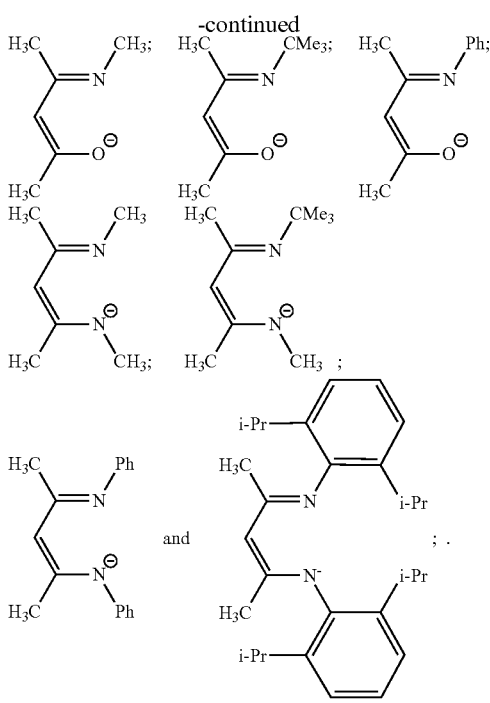

8. The composition according to claim 1 further comprising one or more monomers selected from monomer of formula (VI) or monomer of formula (VII), wherein said monomer of formula (VI) is:

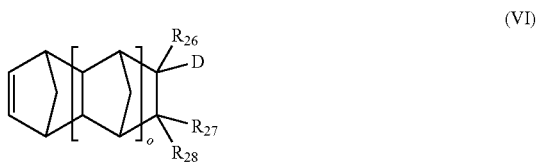

wherein:
o is an integer from 0 to 2, inclusive;
D is $SiR_{29}R_{30}R_{31}$ or a group selected from:

$$-(CH_2)_c-O-SiR_{29}R_{30}R_{31} \qquad (E);$$

$$-(CH_2)_c-SiR_{29}R_{30}R_{31} \qquad (F); \text{ and}$$

$$-(SiR_{29}R_{30})_c-O-SiR_{29}R_{30}R_{31} \qquad (G); \text{ wherein}$$

c is an integer from 1 to 10, inclusive, and where one or more of $CH_2$ is optionally substituted with $(C_1\text{-}C_{10})$alkyl or $(C_1\text{-}C_{10})$perfluoroalkyl;

$R_{26}$, $R_{27}$ and $R_{28}$ are the same or different and independently of each other selected from hydrogen, halogen and hydrocarbyl, where hydrocarbyl is selected from methyl, ethyl, linear or branched $(C_3\text{-}C_{12})$alkyl, $(C_3\text{-}C_{12})$cycloalkyl, $(C_6\text{-}C_{12})$bicycloalkyl, $(C_7\text{-}C_{14})$tricycloalkyl, $(C_6\text{-}C_{10})$aryl, $(C_6\text{-}C_{10})$aryl$(C_1\text{-}C_3)$alkyl, $(C_1\text{-}C_{12})$alkoxy, $(C_3\text{-}C_{12})$cycloalkoxy, $(C_6\text{-}C_{12})$bicycloalkoxy, $(C_7\text{-}C_{14})$tricycloalkoxy, $(C_6\text{-}C_{10})$aryloxy$(C_1\text{-}C_3)$alkyl or $(C_6\text{-}C_{10})$aryloxy; and $R_{29}$, $R_{30}$ and $R_{31}$ are each independently of one another methyl, ethyl, linear or branched $(C_3\text{-}C_9)$alkyl, substituted or unsubstituted $(C_6\text{-}C_{10})$aryl, methoxy ethoxy, linear or branched $(C_3\text{-}C_9)$alkoxy or substituted or unsubstituted $(C_6\text{-}C_{14})$aryloxy;

said monomer of formula (VII) is:

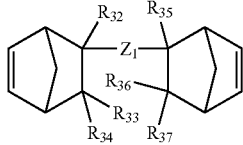

(VII)

wherein:

$Z_1$ is selected from the group consisting of substituted or unsubstituted $(C_1-C_{12})$alkylene, $-(CH_2)_dO(CH_2)_e-$, $-(CH_2)_d(SiR_{38}R_{39})(OSiR_{40}R_{41})_f(CH_2)_e-$ where d, e and f are independently integers from 0 to 6, inclusive, $R_{38}$, $R_{39}$, $R_{40}$ and $R_{41}$ are the same or different and independently of each other selected from methyl, ethyl, linear or branched $(C_3-C_{12})$alkyl, and an arylene selected from the following:

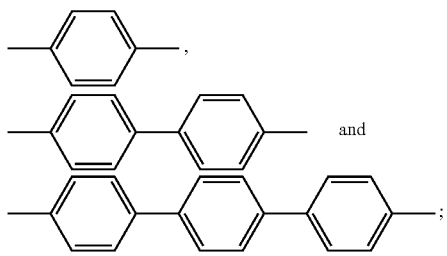

$R_{32}$, $R_{33}$, $R_{34}$, $R_{35}$, $R_{36}$ and $R_{37}$ are the same or different and independently of each other selected from hydrogen, halogen and hydrocarbyl, where hydrocarbyl is selected from methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$alkyl or $(C_6-C_{10})$-aryloxy.

9. The composition according to claim 1, wherein the monomer of formula (V) is selected from the group consisting of:

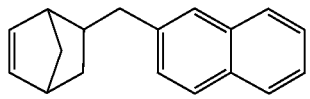

2-(bicyclo[2.2.1]hept-5-en-2-ylmethyl)naphthalene;

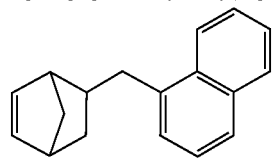

1-(bicyclo[2.2.1]hept-5-en-2-ylmethyl)naphthalene;

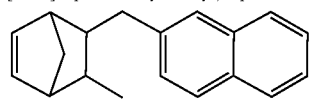

2-((3-methylbicyclo[2.2.1]hept-5-en-2-yl)methyl)naphthalene;

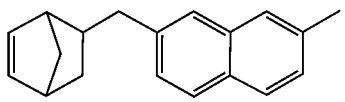

2-(bicyclo[2.2.1]hept-5-en-2-ylmethyl)-7-methylnaphthalene;

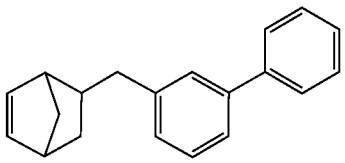

5-([1,1'-biphenyl]-3-ylmethyl)bicyclo[2.2.1]hept-2-ene;

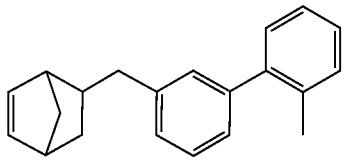

5-((2'-methyl-[1,1'-biphenyl]-3-yl)methyl)bicyclo[2.2.1]hept-2-ene;

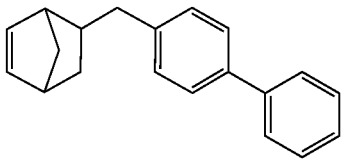

5-([1,1'-biphenyl]-4-ylmethyl)bicyclo[2.2.1]hept-2-ene;

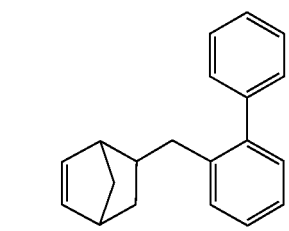

5-([1,1'-biphenyl]-2-ylmethyl)bicyclo[2.2.1]hept-2-ene;

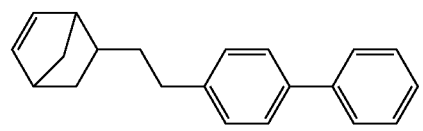

5-(2-([1,1'-biphenyl]4-yl)ethyl)bicyclo[2.2.1]hept-2-ene (NBEtPhPh);

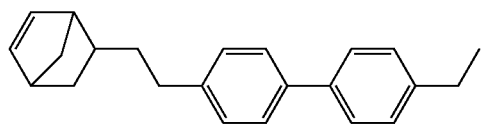

5-(2-(4'-ethyl-[1,1'-biphenyl]-4-yl)ethyl)bicyclo[2.2.1]hept-2-ene;

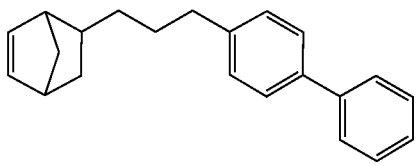

5-(3-([1,1'-biphenyl]-4-yl)propyl)bicyclo[2.2.1]hept-2-ene;

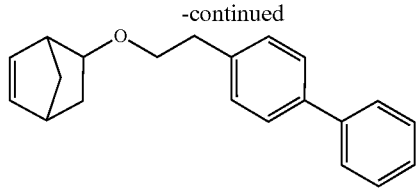

5-(2-([1,1'-biphenyl]-4-yl)ethoxy)bicyclo[2.2.1]hept-2-ene;

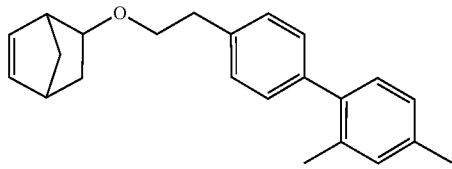

5-(2-(2',4'-dimethyl-[1,1'-biphenyl]-4-yl)ethoxy)bicyclo[2.2.1]hept-2-ene;

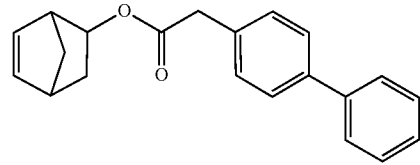

bicyclo[2.2.1]hept-5-en-2-yl 2-([1,1'-biphenyl]-4-yl)acetate;

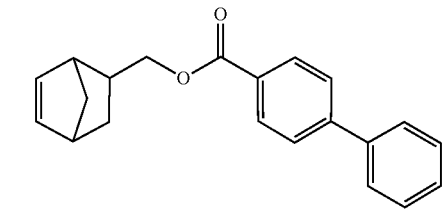

bicyclo[2.2.1]hept-5-en-2-ylmethyl [1,1'-biphenyl]-4-carboxylate;

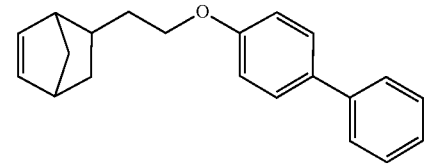

5-(2-([1,1'-biphenyl]-4-yloxy)ethyl)bicyclo[2.2.1]hept-2-ene;

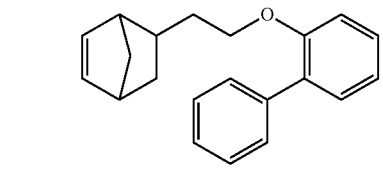

5-(2-([1,1'-biphenyl]-2-yloxy)ethyl)bicyclo[2.2.1]hept-2-ene (NBEtOPhPh);

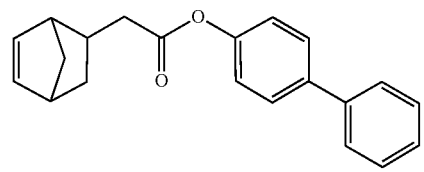

[1,1'-biphenyl]-4-yl 2-(bicyclo[2.2.1]hept-5-en-2-yl)acetate;

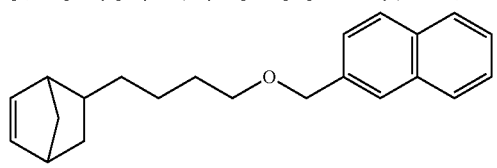

2-((4-(bicyclo[2.2.1]hept-5-en-2-yl)butoxy)methyl)naphthalene;

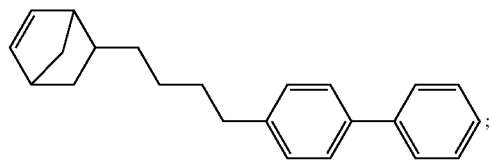

5-(4-([1,1'-biphenyl]-4-yl)butyl)bicyclo[2.2.1]hept-2-ene

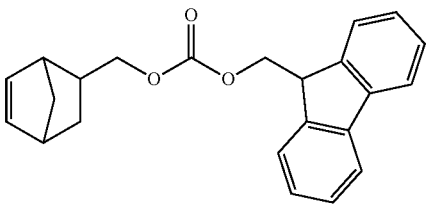

(9H-fluoren-9-yl)methyl (bicyclo[2.2.1]hept-5-en-2-ylmethyl) carbonate;

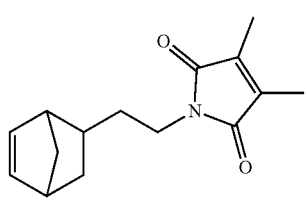

1-(4-bicyclo[2.2.1]hept-5-en-2-ylethyl)-3,4-dimethyl-1H-pyrrole-2,5-dione;

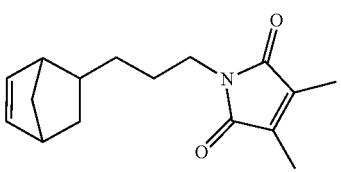

1-(4-bicyclo[2.2.1]hept-5-en-2-ylpropyl)-3,4-dimethyl-1H-pyrrole-2,5-dione;

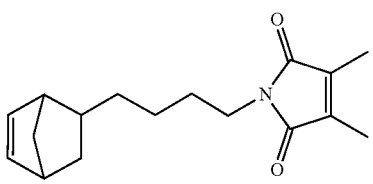

1-(4-bicyclo[2.2.1]hept-5-en-2-ylbutyl)-3,4-dimethyl-1H-pyrrole-2,5-dione;

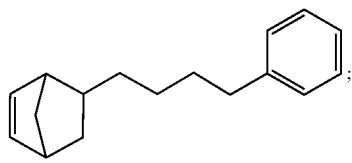

5-(4-phenylbutyl)bicyclo[2.2.1]hept-2-ene

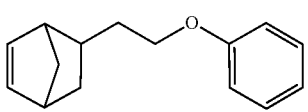

5-(2-phenoxyethyl)bicyclo[2.2.1]hept-2-ene;

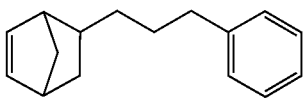

5-(3-phenylpropyl)bicyclo[2.2.1]hept-2-ene;

-continued

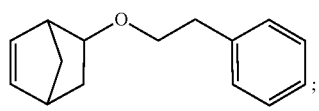

5-phenethoxybicyclo[2.2.1]hept-2-ene

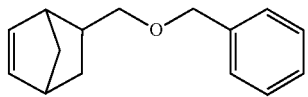

5-((benzyloxy)methyl)bicyclo[2.2.1]hept-2-ene;

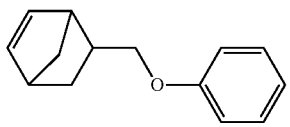

5-(phenoxymethyl)bicyclo[2.2.1]hept-2-ene;

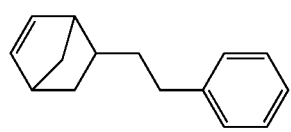

5-phenethylbicyclo[2.2.1]hept-2-ene;

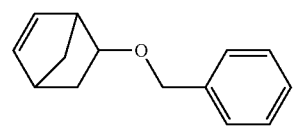

5-(benzyloxy)bicyclo[2.2.1]hept-2-ene;

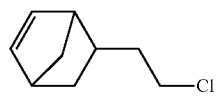

5-(2-chloroethyl)bicyclo[2.2.1]hept-2-ene (NBEtCl);

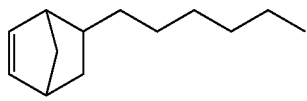

5-hexylbicyclo[2.2.1]hept-2-ene (HexylNB);

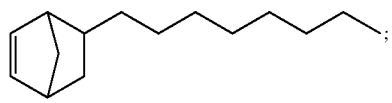

5-octylbicyclo[2.2.1]hept-2-ene (OctNB)

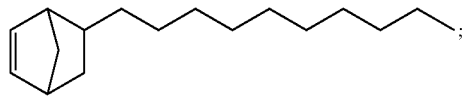

5-decylbicyclo[2.2.1]hept-2-ene (DecNB)

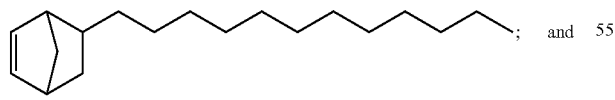

5-dodecylbicyclo[2.2.1]hept-2-ene (DoDecNB)

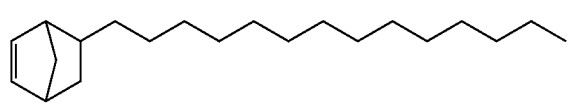

5-tetradecylbicyclo[2.2.1]hept-2-ene (TetraDecNB).

10. The composition according to claim 8, wherein the monomer of formula (VI) or the monomer of formula (VII) is selected from the group consisting of:

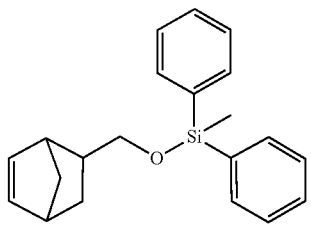

(bicyclo[2.2.1]hept-5-en-2-ylmethoxy)(methyl)diphenylsilane;
(NBCH$_2$OSiMePh$_2$)

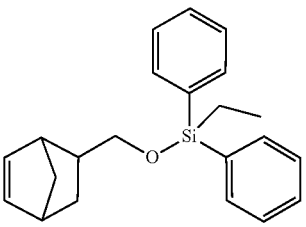

(bicyclo[2.2.1]hept-5-en-2-ylmethoxy)(ethyl)diphenylsilane;

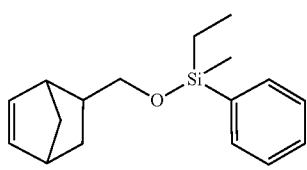

(bicyclo[2.2.1]hept-5-en-2-ylmethoxy)(ethyl)(methyl)(phenyl)silane;

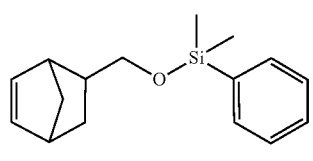

(bicyclo[2.2.1]hept-5-en-2-ylmethoxy)dimethyl(phenyl)silane;

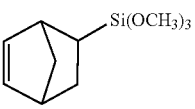

bicyclo[2.2.1]hept-5-en-2-yltrimethoxysilane;

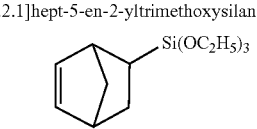

bicyclo[2.2.1]hept-5-en-2-yltriethoxysilane (NBSi(OC$_2$H$_5$)$_3$;

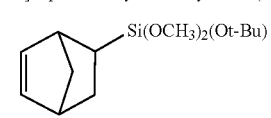

bicyclo[2.2.1]hept-5-en-2-yl(tert-butoxy)dimethoxysilane;

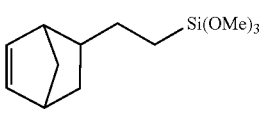

(2-bicyclo[2.2.1]hept-5-en-2-yl)ethyl)trimethoxysilane;

-continued

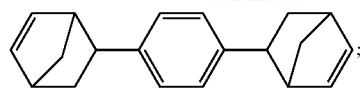

1,4-di(bicyclo[2.2.1]hept-5-en-2-yl)benzene

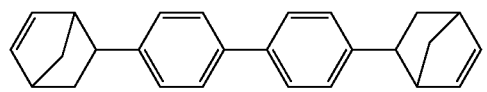

4,4'-di(bicyclo[2.2.1]hept-5-en-2-yl)-1,1'-biphenyl;

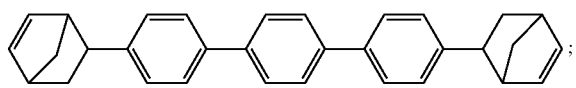

4,4''-di(bicyclo[2.2.1]hept-5-en-2-yl)-1,1':4',1''-terphenyl

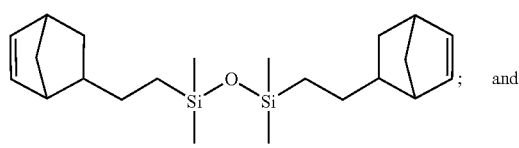 ; and 1,3-bis(norbornenylethyl)-1,1,3,3-tetramethyldisiloxane

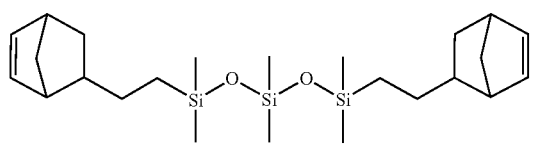

1,5-bis(norbornenylethyl)-1,1,3,3,5,5,-hexamethyltrisiloxane.

11. The composition according to claim 1, wherein the organopalladium compound of formula (III) or the organopalladium compound of formula (IIIA) or the organopalladium compound of formula (IIIB) is selected from the group consisting of:

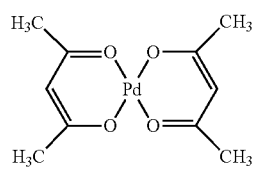

palladium (acetylacetonate)$_2$ (Pd304);

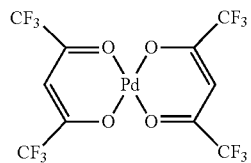

palladium (hexafluoroacetylacetonate)$_2$ (Pd520);

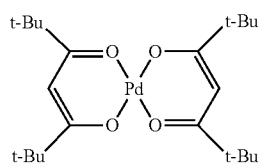

bis(2,2,6,6-tetramethyl-3,5-heptanedionato)palladium(II) (Pd472);

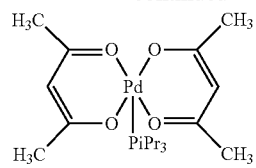

palladium (acetylacetonate)$_2$ tri-isopropylphosphine;

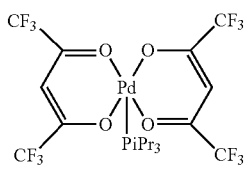

palladium (hexafluoroacetylacetonate)$_2$ tri-isopropylphosphine (Pd680);

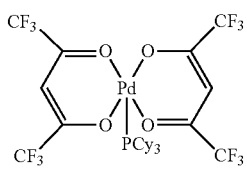

palladium (hexafluoroacetylacetonate)$_2$ tri-cyclohexylphosphine (Pd800);

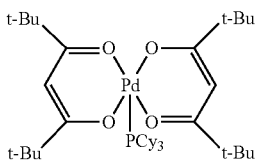

palladium (tetramethylheptanedionate)$_2$ tri-cyclohexylphosphine;

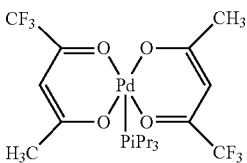

palladium (trifluoroacetylacetonate)$_2$ (Pd(tfacac)$_2$ tri-isopropylphosphine;

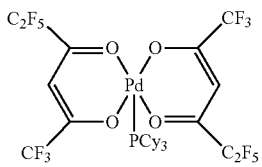

palladium (pentafluoropropionyltrifluoroacetonate)$_2$ ; and
tri-cyclohexylphosphine

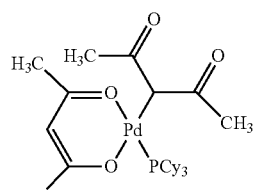

Pd(acac)$_2$PCy$_3$ (Pd585).

12. The composition according to claim 1, wherein the compound of formula (I) or the compound of formula (II) is selected from the group consisting of:

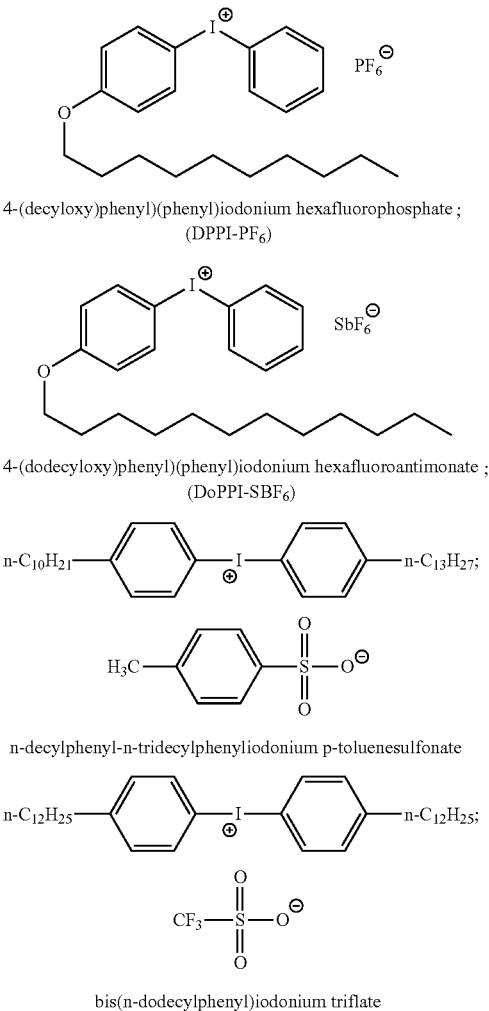

4-(decyloxy)phenyl)(phenyl)iodonium hexafluorophosphate ;
(DPPI-PF$_6$)

4-(dodecyloxy)phenyl)(phenyl)iodonium hexafluoroantimonate ;
(DoPPI-SBF$_6$)

n-decylphenyl-n-tridecylphenyliodonium p-toluenesulfonate bis(n-dodecylphenyl)iodonium triflate where R$_{42}$ and R$_{43}$ are the same or different and each indenpendently ; selected from linear or branched (C$_{10}$-C$_{13}$)alkyl

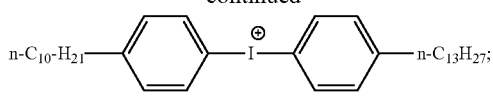

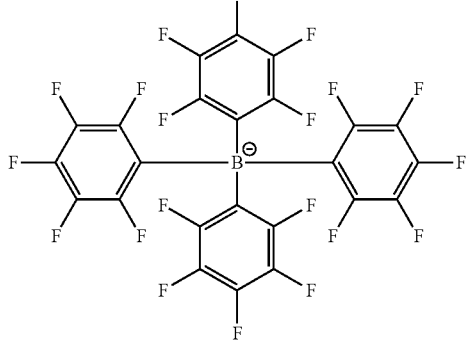

4-n-decyclphenyl-4'-n-tridecylphenyliodonium tetrakis (pentafluorophenyl)borate

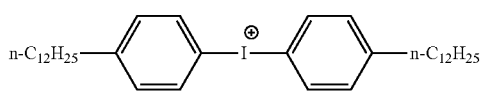

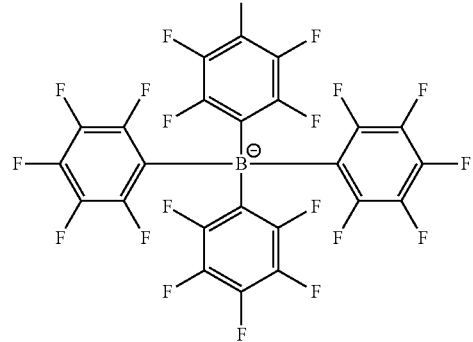

di(4-n-dodecyclphenyl)iodonium tetrakis(pentafluorophenyl)borate ; and
(PAG2)

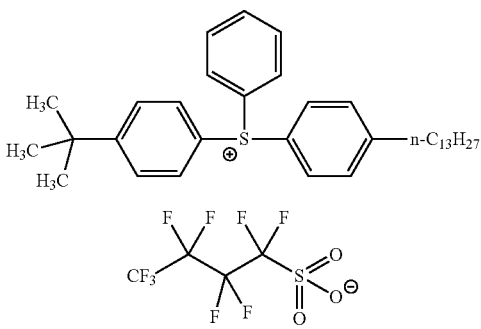

(4-tert-butylphenyl)(phenyl)(4'-tridecylphenyl)sulfonium perfluoro-1-butanesulfonate.

13. The composition according to claim 1, wherein the photosensitizer is a compound of formula (VIII) or a compound of formula (IX):

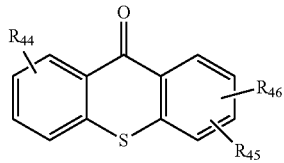

(VIII)

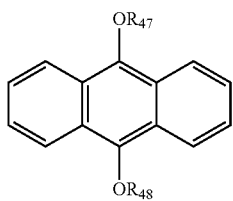

(IX)

wherein

R$_{44}$, R$_{45}$ and R$_{46}$ are the same or different and independently of each other selected from the group consisting of hydrogen, halogen, hydroxy, NO$_2$, NH$_2$, methyl, ethyl, linear or branched (C$_3$-C$_{12}$)alkyl, (C$_3$-C$_{12}$)cycloalkyl, (C$_6$-C$_{12}$)bicycloalkyl, (C$_7$-C$_{14}$)tricycloalkyl, (C$_6$-C$_{10}$)aryl, (C$_6$-C$_{10}$)aryl(C$_1$-C$_3$)alkyl, (C$_1$-C$_{12}$) alkoxy, (C$_3$-C$_{12}$)cycloalkoxy, (C$_6$-C$_{12}$)bicycloalkoxy, (C$_7$-C$_{14}$)tricycloalkoxy, (C$_6$-C$_{10}$)aryloxy(C$_1$-C$_3$)alkyl, (C$_6$-C$_{10}$)-aryloxy, C(O)(C$_1$-C$_6$)alkyl, COOH, C(O)O (C$_1$-C$_6$)alkyl, and SO$_2$(C$_6$-C$_{10}$)aryl;

R$_{47}$ and R$_{48}$ are the same or different and independently of each other selected from the group consisting of methyl, ethyl, linear or branched (C$_3$-C$_{12}$)alkyl, (C$_3$-C$_{12}$)cycloalkyl, (C$_6$-C$_{12}$)bicycloalkyl, (C$_7$-C$_{14}$)tricycloalkyl, (C$_6$-C$_{10}$)aryl and (C$_6$-C$_{10}$)aryl(C$_1$-C$_3$)alkyl.

14. The composition according to claim 1, wherein the compound of formula (VIII) or the compound of formula (IX) is selected from the group consisting of:

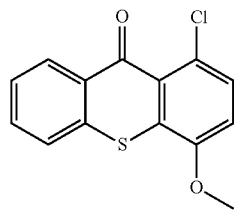

1-chloro-4-methoxy-9H-thioxanthen-9-one;

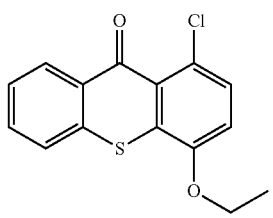

1-chloro-4-ethoxy-9H-thioxanthen-9-one;

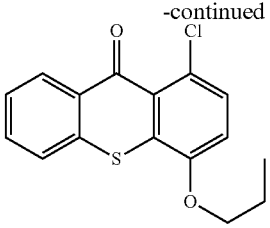

1-chloro-4-propoxy-9H-thioxanthen-9-one;

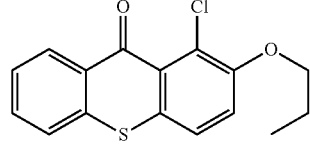

1-chloro-2-propoxy-9H-thioxanthen-9-one;

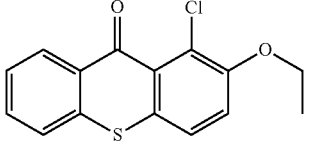

1-chloro-2-ethoxy-9H-thioxanthen-9-one;

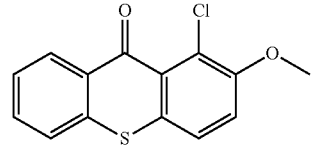

1-chloro-2-methoxy-9H-thioxanthen-9-one;

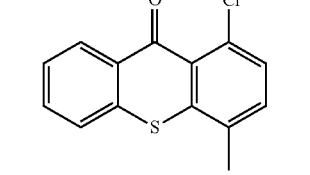

1-chloro-4-methyl-9H-thioxanthen-9-one;

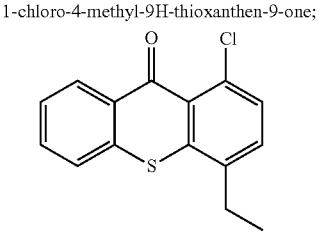

1-chloro-4-ethyl-9H-thioxanthen-9-one;

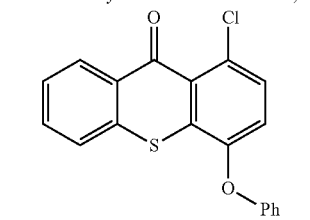

1-chloro-4-phenoxy-9H-thioxanthen-9-one;

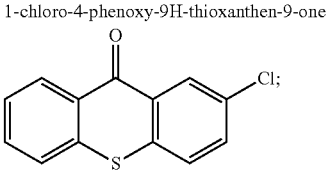

2-chlorothioxanthen-9-one (CTX)

-continued

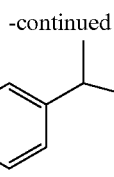

2-isopropyl-9H-thioxanthen-9-one (ITX);

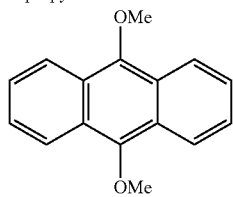

9,10-dimethoxyanthracene (DMA);

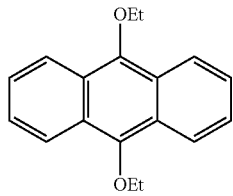

9,10-diethoxyanthracene (DEA); and

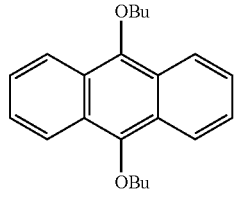

9,10-diethoxyanthracene (DBA).

15. The composition according to claim 1, which is selected from the group consisting of:

5-hexylbicyclo[2.2.1]hept-2-ene (HexylNB), palladium hexafluoroacetylacetonate (Pd520), 4,4'-di-$C_{10-13}$-alkylphenyl derivatives, tetrakis(2,3,4,5,6-pentafluorophenyl)borates (PAG1) and 2-isopropyl-9H-thioxanthen-9-one (ITX);

5-hexylbicyclo[2.2.1]hept-2-ene (HexylNB), 5-(2-([1,1'-biphenyl]-2-yloxy)ethyl)bicyclo[2.2.1]hept-2-ene (NBEtOPhPh), palladium hexafluoroacetylacetonate (Pd520), 4,4'-di-$C_{10-13}$-alkylphenyl derivatives, tetrakis(2,3,4,5,6-pentafluorophenyl)borates (PAG1) and 2-isopropyl-9H-thioxanthen-9-one (ITX);

5-decylbicyclo[2.2.1]hept-2-ene (DecNB), 5-(2-([1,1'-biphenyl]-2-yloxy)ethyl)bicyclo[2.2.1]hept-2-ene (NBEtOPhPh), bis(2,2,6,6-tetramethyl-3,5-heptanedionato)palladium(II) (Pd472), bis(4-n-dodecylphenyl)iodonium tetrakis(pentafluorophenyl)borate (PAG2) and 2-chloro-9H-thioxanthen-9-one (CTX);

5-decylbicyclo[2.2.1]hept-2-ene (DecNB), bis(2,2,6,6-tetramethyl-3,5-heptanedionato)palladium(II) (Pd472), di(4-n-dodecylphenyl)iodonium tetrakis(pentafluorophenyl)borate (PAG2) and 2-chloro-9H-thioxanthen-9-one (CTX); and 5-hexylbicyclo[2.2.1]hept-2-ene (HexylNB), palladium hexafluoroacetylacetonate (Pd520), di(4-n-dodecylphenyl)iodonium tetrakis(pentafluorophenyl)borate (PAG2) and 2-isopropyl-9H-thioxanthen-9-one (ITX).

16. A kit for forming a substantially transparent film comprising:

a) a soluble photoacid generator selected from the group consisting of a compound of formula (I):

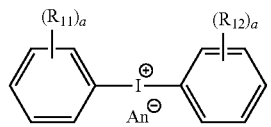

and a compound of formula (II):

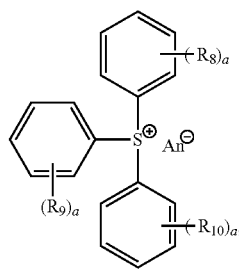

wherein:

a is an integer from 1 to 5;

$An^{\ominus}$ is selected from the group consisting of $Cl^{\ominus}$, $Br^{\ominus}$, $I^{\ominus}$, $BF_4^{\ominus}$, tetrakis(pentafluorophenyl)borate, tetrakis(3,5-bis(trifluoromethyl)phenyl)borate, tetrakis(2-fluorophenyl)borate, tetrakis(3-fluorophenyl)borate, tetrakis(4-fluorophenyl)borate, tetrakis(3,5-difluorophenyl)borate, tetrakis(2,3,4,5-tetrafluorophenyl)borate, tetrakis(3,4,5,6-tetrafluorophenyl)borate, tetrakis(3,4,5-trifluorophenyl)borate, methyltris(perfluorophenyl)borate, ethyltris(perfluorophenyl)borate, phenyltris(perfluorophenyl)borate, tetrakis(1,2,2-trifluoroethylenyl)borate, tetrakis(4-tri-1-propylsilyltetrafluorophenyl)borate, tetrakis(4-dimethyl-tert-butylsilyltetrafluorophenyl)borate, (triphenylsiloxy)tris(pentafluorophenyl)borate, (octyloxy)tris(pentafluorophenyl)borate, tetrads[3,5-bis[1-methoxy-2,2,2-trifluoro-1-(trifluoromethyl)ethyl]pheny-l]borate, tetrakis[3-[1-methoxy-2,2,2-trifluoro-1-(trifluoromethyl)ethyl]-5-(trifluoromethyl)phenyl]borate, and tetrakis[3-[2,2,2-trifluoro-1-(2,2,2-trifluoroethoxy)-1-(trifluoromethyl)-ethyl]-5-(trifluoromethyl)phenyl]borate, $PF_6^{\ominus}$, $SbF_6^{\ominus}$, n-$C_4F_9SO_3^{\ominus}$, $CF_3SO_3^{\ominus}$ and p-$CH_3(C_6H_4)$—$SO_3^{\ominus}$;

at least one of $R_8$, $R_9$, $R_{10}$, $R_{11}$ and $R_{12}$ is selected from the group consisting of linear or branched ($C_{10}$-$C_{20}$) alkyl, ($C_6$-$C_{10}$)aryl($C_{10}$-$C_{20}$)alkyl, ($C_{10}$-$C_{20}$)alkoxy, ($C_6$-$C_{10}$)aryloxy($C_{10}$-$C_{20}$)alkyl, ($C_{10}$-$C_{20}$)alkanoyl($C_6$-$C_{10}$)aryl and ($C_{10}$-$C_{20}$)alkoxy($C_6$-$C_{10}$)aroyl($C_6$-$C_{20}$)alkyl; and the remaining $R_8$, $R_9$, $R_{10}$, $R_{11}$ and $R_{12}$ are the same or different and each independently selected from the group consisting of halogen, methyl, ethyl, linear or branched ($C_3$-$C_{20}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_3$)alkyl, ($C_1$-$C_{12}$)alkoxy, ($C_3$-$C_{12}$)cycloalkoxy, ($C_6$-$C_{12}$)bicycloalkoxy, ($C_7$-$C_{14}$)

tricycloalkoxy, $(C_6\text{-}C_{10})$aryloxy$(C_1\text{-}C_3)$alkyl, $(C_6\text{-}C_{10})$-aryloxy, $(C_6\text{-}C_{10})$thioaryl, $(C_1\text{-}C_6)$alkanoyl$(C_6\text{-}C_{10})$thioaryl, $(C_1\text{-}C_6)$alkoxy$(C_6\text{-}C_{10})$aroyl$(C_1\text{-}C_6)$alkyl and $(C_6\text{-}C_{10})$thioaryl-$(C_6\text{-}C_{10})$diarylsulfonium salt;
b) an organopalladium compound selected from the group consisting of a compound of formula (III), a compound of formula (IIIA) and a compound of formula (IIIB):

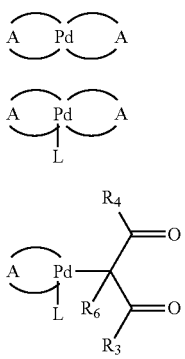

(III)

(IIIA)

(IIIB)

wherein:
L is a ligand selected from the group consisting of $P(R)_3$, $P(OR)_3$, $O=P(R)_3$, RCN and substituted or unsubstituted pyridines, where R is selected from the group consisting of methyl, ethyl, linear or branched $(C_3\text{-}C_{16})$ alkyl, $(C_1\text{-}C_{16})$perfluoroalkyl, $(C_3\text{-}C_{10})$cycloalkyl, $(C_6\text{-}C_{10})$aryl$(C_1\text{-}C_{16})$alkyl and substituted or unsubstituted $(C_6\text{-}C_{10})$aryl;
each A independently is a bidentate monoanionic ligand of formula (IV):

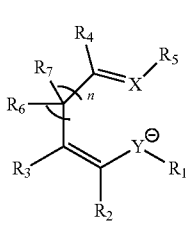

(IV)

wherein:
n is an integer 0, 1 or 2;
X and Y are independently of each other selected from O, N and S;
$R_1$, $R_2$, $R_3$, $R_4$, $R_5$, $R_6$ and $R_7$ are the same or different and each independently selected from the group consisting of hydrogen, methyl, ethyl, linear or branched $(C_3\text{-}C_{16})$ alkyl, $(C_1\text{-}C_{16})$perfluoroalkyl, $(C_3\text{-}C_{10})$cycloalkyl, $(C_6\text{-}C_{10})$aryl$(C_1\text{-}C_{16})$alkyl and substituted or unsubstituted $(C_6\text{-}C_{10})$aryl; provided when either X or Y is O or S, $R_1$ and $R_5$, respectively, do not exist;
c) one or more olefinic monomers of the formula (V):

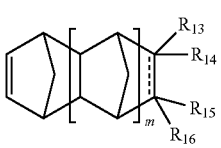

(V)

wherein:
m is an integer 0, 1 or 2;
----- is a single bond or a double bond;
at least one of $R_{13}$, $R_{14}$, $R_{15}$ and $R_{16}$ is selected from the group consisting of linear or branched $(C_6\text{-}C_{16})$alkyl, $(C_6\text{-}C_{12})$aryl$(C_1\text{-}C_{16})$alkyl, $(C_6\text{-}C_{10})$aryloxy$(C_2\text{-}C_{16})$ alkyl and $(C_6\text{-}C_{10})$aryl$(C_6\text{-}C_{10})$aryloxy$(C_1\text{-}C_{16})$alkyl;
the remaining $R_{13}$, $R_{14}$, $R_{15}$ and $R_{16}$ are the same or different and each independently selected from the group consisting of hydrogen, halogen, a hydrocarbyl or halohydrocarbyl group selected from methyl, ethyl, linear or branched $(C_3\text{-}C_{16})$alkyl, perfluoro$(C_1\text{-}C_{12})$ alkyl, $(C_3\text{-}C_{12})$cycloalkyl, $(C_6\text{-}C_{12})$bicycloalkyl, $(C_7\text{-}C_{14})$tricycloalkyl, $(C_6\text{-}C_{10})$aryl, $(C_6\text{-}C_{10})$aryl$(C_1\text{-}C_6)$alkyl, perfluoro$(C_6\text{-}C_{10})$aryl, perfluoro$(C_6\text{-}C_{10})$aryl$(C_1\text{-}C_6)$alkyl, methoxy, ethoxy, linear or branched $(C_3\text{-}C_{16})$ alkoxy, perfluoro$(C_1\text{-}C_{12})$alkoxy, $(C_3\text{-}C_{12})$cycloalkoxy, $(C_6\text{-}C_{12})$bicycloalkoxy, $(C_7\text{-}C_{14})$tricycloalkoxy, $(C_6\text{-}C_{10})$aryloxy, $(C_6\text{-}C_{10})$aryl$(C_1\text{-}C_6)$alkoxy, perfluoro$(C_6\text{-}C_{10})$aryloxy, perfluoro$(C_6\text{-}C_{10})$aryl$(C_1\text{-}C_3)$alkoxy, a group of formula (A):

—Z—Aryl; (A)

a group of formula (A1):

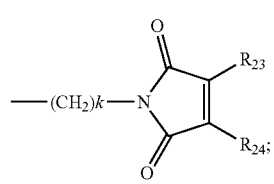

(A1)

a group of formula (A2):

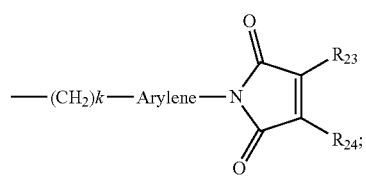

(A2)

a group of formula (A3):

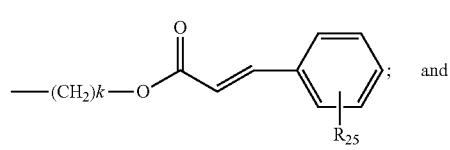

(A3)

and a group of formula (A4):

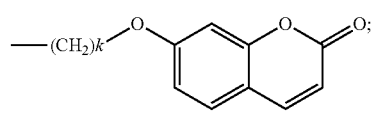

(A4)

wherein:
Z is selected from the group consisting of:
O, CO, C(O)O, OC(O), OC(O)O, S, $(CR_{17}R_{18})_b$, $O(CR_{17}R_{18})_b$, $O(CR_{17}R_{18})_bO$, $C(O)(CR_{17}R_{18})_b$, $(CR_{17}R_{18})_bC(O)$, $C(O)O(CR_{17}R_{18})_b$, $(CR_{17}R_{18})_bC(O)O$, $OC(O)(CR_{17}R_{18})_b$, $(CR_{17}R_{18})_bOC(O)$, $(CR_{17}R_{18})_bOC(O)O$, $(CR_{17}R_{18})_bOC(O)O(CR_{17}R_{18})_b$, $OC(O)O(CR_{17}R_{18})_b$, $S(CR_{17}R_{18})_b$, $(CR_{17}R_{18})_bS$, $(SiR_{17}R_{18})_b$, $O(SiR_{17}R_{18})_b$, $(SiR_{17}R_{18})_bO$, where $R_{17}$ and $R_{18}$ are the same or different and each independently selected from hydrogen, methyl, ethyl, linear or branched $(C_3-C_{12})$alkyl, substituted or unsubstituted $(C_6-C_{14})$aryl, methoxy, ethoxy, linear or branched $(C_3-C_6)$alkyloxy, $(C_2-C_6)$acyl, $(C_2-C_6)$acyloxy, and substituted or unsubstituted $(C_6-C_{14})$aryloxy; and b is an integer from 0 to 12, inclusive;

Aryl is selected from the group consisting of substituted or unsubstituted phenyl, substituted or unsubstituted biphenyl and substituted or unsubstituted naphthyl, substituted or unsubstituted terphenyl, substituted or unsubstituted anthracenyl substituted or unsubstituted fluorenyl, wherein said substituents are selected from the group consisting of halogen, methyl, ethyl, linear or branched $(C_3-C_6)$alkyl, perfluoro$(C_1-C_{12})$alkyl, $(C_3-C_{12})$cycloalkyl, $(C_6-C_{10})$aryl, $(C_6-C_{10})$aryl$(C_1-C_6)$alkyl, perfluoro$(C_6-C_{10})$aryl, perfluoro$(C_6-C_{10})$aryl$(C_1-C_6)$alkyl, methoxy, ethoxy, linear or branched $(C_3-C_{16})$alkoxy, perfluoro$(C_1-C_{12})$alkoxy, $(C_3-C_{12})$cycloalkoxy, $(C_6-C_{10})$aryloxy, $(C_6-C_{10})$aryl$(C_1-C_6)$alkoxy, perfluoro $(C_6-C_{10})$aryloxy and perfluoro$(C_6-C_{10})$aryl$(C_1-C_3)$alkoxy;

k is an integer from 1 to 12;

$R_{23}$, $R_{24}$ and $R_{25}$ are the same or different and each independently selected from the group consisting of hydrogen, methyl, ethyl, linear or branched $(C_3-C_{12})$ alkyl, perfluoro$(C_1-C_{12})$alkyl, methoxy, ethoxy, linear or branched $(C_3-C_{12})$alkoxy, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_6)$alkyl, perfluoro$(C_6-C_{10})$aryl and perfluoro$(C_6-C_{10})$aryl$(C_1-C_6)$alkyl; or $R_{23}$ and $R_{24}$ taken together with the intervening carbon atoms to which they are attached to form a substituted or unsubstituted $(C_5-C_{14})$cyclic, $(C_5-C_{14})$bicyclic or $(C_5-C_{14})$tricyclic ring; and Arylene is substituted or unsubstituted bivalent $(C_6-C_{14})$aryl;

or one of $R_1$ and $R_2$ taken together with one of $R_3$ and $R_4$ and the carbon atoms to which they are attached to form a substituted or unsubstituted $(C_5-C_{14})$cyclic, $(C_5-C_{14})$bicyclic or $(C_5-C_{14})$tricyclic ring;

and a) a photosensitizer.

17. The kit according to claim 16, which contains at least two distinct first and second monomers of formula (V), wherein the first monomer and the photoacid generator are completely soluble in the second monomer, and when said composition is exposed to suitable actinic radiation for a sufficient length of time it forms a substantially transparent film having at least 90 percent of visible light transmission.

18. The kit according to claim 16, which is selected from the group consisting of:

5-hexylbicyclo[2.2.1]hept-2-ene (HexylNB), palladium hexafluoroacetylacetonate (Pd520), 4,4'-di-$C_{10-13}$-alkylphenyl derivatives, tetrakis(2,3,4,5,6-pentafluorophenyl)borates (PAG1) and 2-isopropyl-9H-thioxanthen-9-one (ITX);

5-hexylbicyclo[2.2.1]hept-2-ene (HexylNB), 5-(2-([1,1'-biphenyl]-2-yloxy)ethyl)bicyclo[2.2.1]hept-2-ene (NBEtOPhPh), palladium hexafluoroacetylacetonate (Pd520), 4,4'-di-$C_{10-13}$-alkylphenyl derivatives, tetrakis(2,3,4,5,6-pentafluorophenyl)borates (PAG1) and 2-isopropyl-9H-thioxanthen-9-one (ITX);

5-decylbicyclo[2.2.1]hept-2-ene (DecNB), 5-(2-([1,1'-biphenyl]-2-yloxy)ethyl)bicyclo[2.2.1]hept-2-ene (NBEtOPhPh), bis(2,2,6,6-tetramethyl-3,5-heptanedionato)palladium(II) (Pd472), bis(4-n-dodecylphenyl)iodonium tetrakis(pentafluorophenyl)borate (PAG2) and 2-chloro-9H-thioxanthen-9-one (CTX);

5-decylbicyclo[2.2.1]hept-2-ene (DecNB), bis(2,2,6,6-tetramethyl-3,5-heptanedionato)palladium(II) (Pd472), di(4-n-dodecylphenyl)iodonium tetrakis(pentafluorophenyl)borate (PAG2) and 2-chloro-9H-thioxanthen-9-one (CTX); and 5-hexylbicyclo[2.2.1]hept-2-ene (HexylNB), palladium hexafluoroacetylacetonate (Pd520), di(4-n-dodecylphenyl)iodonium tetrakis(pentafluorophenyl)borate (PAG2) and 2-isopropyl-9H-thioxanthen-9-one (ITX).

19. A film formed from the composition of claim 1.

20. The film formed according to claim 16.

* * * * *